(12) United States Patent
Sasaki et al.

(10) Patent No.: US 7,868,137 B2
(45) Date of Patent: Jan. 11, 2011

(54) SEARCH FOR CANCER MARKERS BY A NOVEL SCREENING METHOD

(75) Inventors: Kazuki Sasaki, Tokyo (JP); Kae Sato, Tokyo (JP); Ken Yamaguchi, Tokyo (JP)

(73) Assignees: Japan as represented by President of National Cancer Center, Tokyo (JP); Advanced Life Science Institute, Inc., Saitama (JP)

( * ) Notice: Subject to any disclaimer, the term of this patent is extended or adjusted under 35 U.S.C. 154(b) by 749 days.

(21) Appl. No.: 11/704,252

(22) Filed: Feb. 9, 2007

(65) Prior Publication Data

US 2008/0020404 A1    Jan. 24, 2008

Related U.S. Application Data

(62) Division of application No. 10/490,471, filed as application No. PCT/JP02/07982 on Aug. 5, 2002, now abandoned.

(30) Foreign Application Priority Data

Sep. 25, 2001  (JP)  ............... 2001-292348
May 16, 2002   (JP)  ............... 2002-141959

(51) Int. Cl.
    *A61K 38/00*  (2006.01)
(52) U.S. Cl. .................................... 530/326
(58) Field of Classification Search ............. None
    See application file for complete search history.

(56) References Cited

U.S. PATENT DOCUMENTS 3,592,836 A *  7/1971  Hoffmann et al. ........... 558/282
6,346,606 B1   2/2002  Mollenhauser et al.
6,670,195 B1 * 12/2003 Ghiso et al. ................. 436/513

FOREIGN PATENT DOCUMENTS

| JP | 55-64799 | 5/1980 |
|----|----------|--------|
| JP | 58-89196 | 5/1983 |
| WO | WO 98/30687 | 7/1998 |
| WO | WO 99/25825 | 5/1999 |
| WO | WO 00/55350 | 9/2000 |
| WO | WO 00/58357 | 10/2000 |
| WO | WO 00/71671 | 11/2000 |
| WO | WO 02/42733 | 5/2002 |

OTHER PUBLICATIONS

Pharmacia Biotech, 1997 catalog pages.*

K. Gevaert et al., "Protein indentification methods in proteomics", *Electrophoresis*, 2000, vol. 21, pp. 1145-1154.

Ball et al., "An integrated approach utilizing artificial neural networks and SELDI mass spectrometry for the classification of human tumours and rapid identification of potential biomarkers," Bioinformatics, Mar. 2002, vol. 18, No. 3, pp. 395-404.

Chapman, K., "The ProteinChip® Biomarker System from Ciphergen Biosystems: a novel proteomics platform for rapid biomarker discovery and validation," Biochemical Society Transactions, Apr. 2002, vol. 30, No. 2, pp. 82-87.

Li et al., "Proteomics and Bioinformatics Approaches for Identification of Serum Biomarkers to Detect Breast Cancer," Clinical Chemistry, Aug. 2002, vol. 48, No. 8, pp. 1296-1304.

Petricoin III et al., "Use of proteomic patterns in serum to identify ovarian cancer," The Lancet, Feb. 16, 2002, pp. 572-577.

Sato et al., "Mass spectrometric high-throughput analysis of serum-free conditioned medium from cancer cell lines," Cancer Letters, Sep. 20, 2001, vol. 170, No. 2, pp. 153-159.

Sato et al., "Peptide differential display of serum-free conditioned medium from cancer cell lines," Cancer Letters, Feb. 25, 2002, vol. 176, No. 2, pp. 199-203.

Von Eggeling et al., "Mass spectrometry meets chip technology: A new proteomic tool in cancer research?", Electrophoresis, Aug. 2001, vol. 22, No. 14, pp. 2898-2902.

Mollenhauer et al., "DMBT1, a new member of the SRCR superfamily, on chromosome 10q25.3-26.1 is deleted in malignant brain tumours", Nature Genetics, Sep. 1997, vol. 17, No. 1, pp. 32-39.

Rosty et al., "Identification of Hepatocarcinoma-Intestine-Pancreas/Pancreatitis-associated Protein I as a Biomarker for Pancreatic Ductal Adnocarcinoma by Protein Biochip Technology", Cancer Research, Mar. 2002, vol. 62, No. 2, pp. 1868-1875.

Sasaki et al, "Peptidomics-based Approach Reveals the Secretion of the 29-Residue COOH-Terminal Fragment of the Putative Tumor Suppressor Protein DMBT1 from Pancreatic Adenocarcinoma Cell Lines", Cancer Research, Sep. 2002, vol. 62, No. 17, pp. 4894-4898.

Robert K. Scopes, "Protein Purification: Principles and Practice", $2^{nd}$ Edition (1987), pp. 100-118.

* cited by examiner

*Primary Examiner*—Cecilia Tsang
*Assistant Examiner*—Thomas S Heard
(74) *Attorney, Agent, or Firm*—Foley & Lardner LLP

(57) ABSTRACT

The present invention relates to a method of concentrating low molecular weight peptides in the supernatant of serum-free cultured cells, said method comprising allowing the peptides to bind to a strong cation exchanger under an acid condition, and eluting them under an alkali condition to concentrate the peptide. Furthermore, peptides having the amino acid sequence as set forth in SEQ ID NO: 1 or 2, and a method of screening cancer markers using antibody to these peptides, are disclosed.

2 Claims, 13 Drawing Sheets

SEARCH FOR CANCER MARKERS BY A NOVEL SCREENING METHOD

CROSS-REFERENCE TO RELATED APPLICATIONS

This application is a divisional application of U.S. patent application Ser. No. 10/490,471, filed Mar. 24, 2004 now abandoned, which is the national stage application filed under 35 U.S.C. §371 of International Application No. PCT/JP02/07982, filed Aug. 5, 2002, which claims priority from Japanese patent applications 2001-292348 and 2002-141959, filed Sep. 25, 2001, and May 16, 2002, respectively.

FIELD OF THE INVENTION

The present invention relates to a peptide concentration method, based on a one-step sample preparation method, for the detection of low molecular weight peptides secreted from cultured cells into a serum-free medium, and a differential display method based on matrix assisted mass spectrometry, a novel method of screening cancer markers using such a method, peptides that could be pancreatic cancer markers detected by said screening method, antibodies to said peptides, hybridomas that produce said antibodies, a diagnostic reagent comprising said antibody, and the like.

Background Art

Pancreatic cancer is a tumor that develops at the retroperitoneal space, a position clinically difficult to be detected. Thus, conventionally, it was often found at a stage when treatment is difficult, and was considered an intractable tumor. Diagnostic methods have made a great progress due to diagnostic imaging such as US, CT and MRI, and endoscopy based on recent technological innovation. Despite these advances in diagnostic methods, treatment results of pancreatic cancer have been below expectations. Excision rates and prognosis of tumors 2 cm or larger are both poor, and rates of discovery are low for cases of small pancreatic cancers (T1) 2 cm or smaller with better excision rates, and, for the cases that were detected, Stage I cases account for less than 50% with the half or more already being at the stage of advanced cancer. In order to enhance the treatment results of this pancreatic cancer, it is important to discover small cancers at early stages.

For the early discovery of pancreatic cancer, early diagnosis of pancreatic cancer is important, and diagnostic methods for detecting pancreatic cancer at present include the above-mentioned diagnostic imaging such as US, CT and MRI, and measurement of serum enzymes and tumor markers. The measurement of serum enzymes and tumor markers is very important for the discovery of pancreatic cancer, but lacks cancer specificity because pancreatic enzymes in the blood increase with the inflammation of the pancreas.

Furthermore, though a sugar chain antigen such as CA19-9, a tumor marker, is useful as a marker for the diagnosis and monitoring of progressive pancreatic cancer, its usefulness in early diagnosis is not satisfactory. In addition to CA19-9, it has been reported, CEA, ST-439, sialyl SSEA-1 (SLX), DU-PAN-2, CA-125, CA-50 etc. are useful as tumor markers; all of them, however, are sugar chain antigens, and are not substances specifically secreted from a cancer of the pancreas. The problem, therefore, is the low specificity of markers for pancreatic cancer.

Conventionally, tumor markers specific for certain tumors have been isolated and identified from the serum of cancer patients and cells established from cancer tissues. For such isolation and identification, these potential marker substances had to be obtained in large quantities, and a large quantity of samples was needed, from which trace amounts of markers had to be detected. Thus, it was only possible to detect substances that are present in large quantities in test samples.

Peptides or low molecular weight proteins selectively secreted from cancer cells could serve as tumor markers. This hypothesis became a reality when the present inventors demonstrated that gastrin-releasing peptide precursor (proGRP) is useful as a tumor marker specific for small cell lung carcinoma (SCLC) [Miyake et al., Cancer Res. 54:2136-2140 (1996)]. The present inventors have studied the production of a series of peptides by radioimmunoassay (RIA), and demonstrated that GRP is selectively recognized in SCLC [Yamaguchi et al., Recent Results Cancer Res. 99:107-116 (1985)].

By determining proGRP, a precursor of GRP, the present inventors demonstrated that it can be used as a marker for early detection of SCLC and for therapeutic effects, which have been granted patents (U.S. Pat. No. 2,925,479, U.S. Pat. No. 3,210,994). However, the method that discovered the usefulness of this proGRP as a tumor marker is one in which sera of patients with SCLC and sera of patients with non-SCLC are measured by RIA, and thus it is necessary to generate many different antibodies and to carry out the determination of a multitude of samples, requiring a large amount of time and effort. In addition, new peptide candidates cannot be found by this method.

DISCLOSURE OF THE INVENTION

The present invention provides a method for efficiently screening novel pancreatic cancer markers by a method, for discovering low molecular weight peptides that could be pancreatic cancer markers, which comprises combining a one-step sample preparation and matrix assisted mass spectrometry. The present invention also provides markers for diagnosing pancreatic cancer that was discovered using such a screening method.

Serum-free culture supernatant derived from a cancer cell line are favorable starting materials for searching for tumor markers. Such materials contain protein-derived peptide fragments and/or secretory peptides including tumor markers that are currently used in clinical practices. When a proteomics approach is adopted to discover marker peptides, it is naturally necessary to use a differential display strategy other than a two-dimensional electrophoresis, in order to compare profiles of secretory peptides in two or more culture supernatants, because standard electrophoresis cannot resolve and detect peptides of 10,000 daltons or smaller.

In order to solve the above problems, the present invention provides a method of concentrating low molecular weight peptides in the supernatant of serum-free cultured cells, said method comprising:

a) allowing the peptides to bind to a strong cation exchanger under an acid condition, and b) eluting them under an alkali condition to concentrate the peptides.

The present invention also provides a method of screening peptides that are specifically secreted from a certain cultured cell line, said method comprising concentrating peptides in two or more culture supernatants by the method according to claim 1, and then comparatively analyzing them using a mass spectrometer.

The present invention also provides a secretory peptide comprising part or all of an amino acid sequence that is substantially identical to the amino acid sequence as set forth in SEQ ID NO: 1. This peptide is preferably a secretory peptide comprising part or all of the amino acid sequence as set forth in SEQ ID NO: 1.

The present invention also provides a peptide comprising part or all of an amino acid sequence that is substantially identical to the amino acid sequence as set forth in SEQ ID NO: 2. This peptide is preferably a secretory peptide comprising part or all of the amino acid sequence as set forth in SEQ ID NO: 2.

Any of the above peptides is a secretory peptide secreted from the pancreatic cancer cells and is characterized by serving as a pancreatic cancer marker.

The present invention further provides a method of detecting or quantitating any of the above peptides.

The present invention further provides a diagnostic kit or a diagnostic reagent for diagnosing pancreatic cancer by detecting or quantitating any of the above peptides.

The present invention also provides an antibody that has a binding affinity for any of the above peptides. This antibody is, for example, a polyclonal antibody or a monoclonal antibody.

The present invention further provides a hybridoma that produces the above monoclonal antibody.

The present invention also provides the above measurement method that uses the above antibody.

The present invention further provides a diagnostic kit or a diagnostic reagent comprising the above antibody.

BEST MODE FOR CARRYING OUT THE INVENTION

Figure 1:
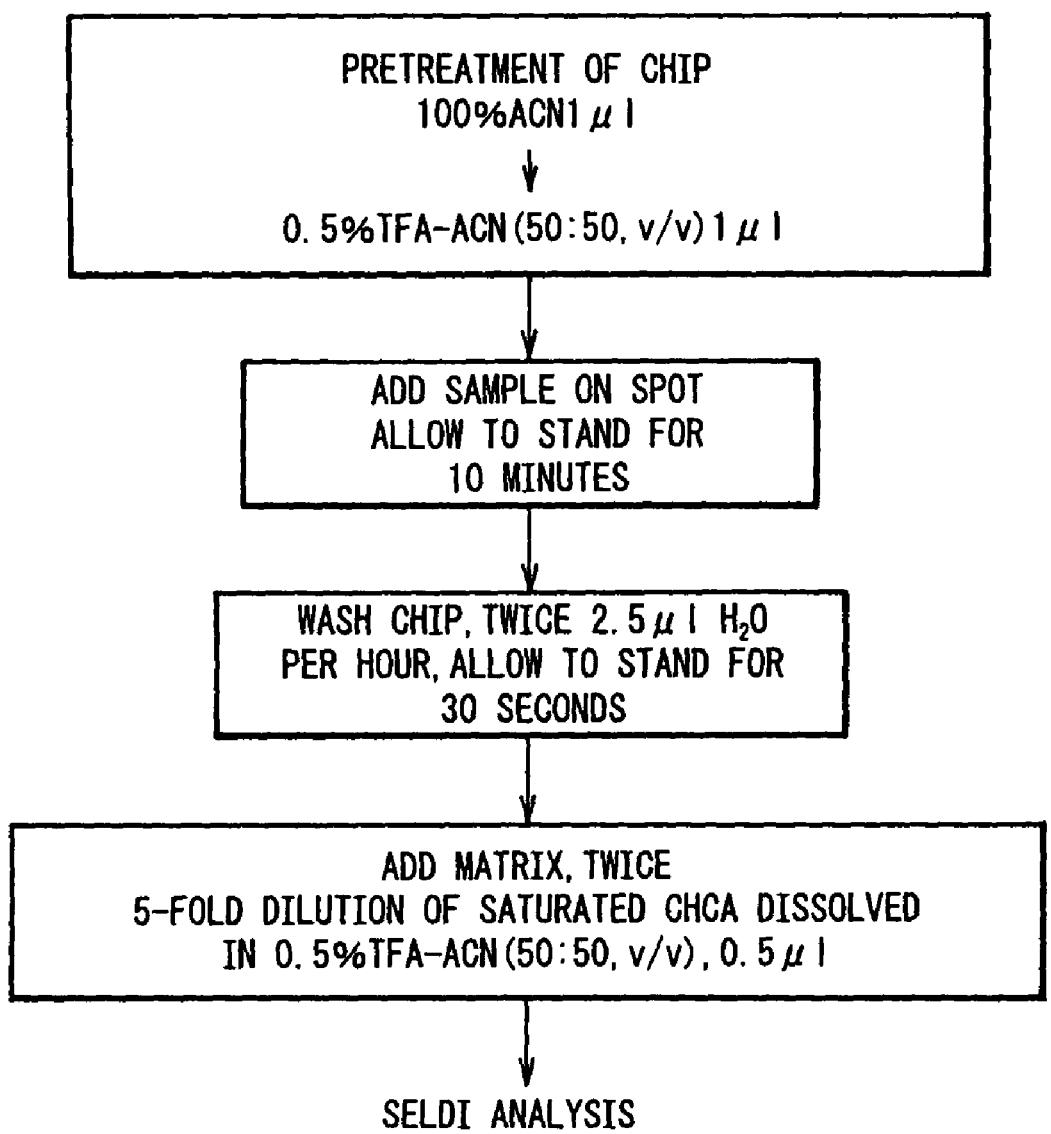
FIG. 1 shows a protocol for the H4 protein chip that has been optimized for profiling of low molecular weight proteins in the culture supernatant.

Considering recent advances in Matrix Assisted Laser Desorption/Ionization (MALDI) mass spectrometry, this technique, that offers molecular mass with incomparable precision, can be applied [Current Protocols in Molecular Biology, John Wiley & Sons, Inc., New York Units 10. 21 (1997)]. Information on molecular mass obtained by the mass spectrometry will be so precise as to enable finding characteristic molecules, on one hand, and to exclude molecules expressed in common, on the other hand. Although the MALDI mass spectrometry has excellent sensitivity as well, the problems associated with sample preparation cannot be avoided [Gobom et al., J. Mass Spectrom. 34:105-116 (1999)].

It is also possible to use the technology of surface-enhanced laser desorption ionization (SELDI) mass spectrometry protein chip, an type of affinity MALDI mass spectrometry. The SELDI protein chip has been fabricated to affinity-capture a variety of proteins present in biological materials, and by so doing non-purified raw samples may also be analyzed [Hutchens et al., Rapid Commun, Mass Spectrom 7:576-580 (1993), Merchant et al., Electrophoresis 21:1164-1177 (2000)].

As starting materials for biomarker search, the present inventors have used serum-free culture supernatants of cultured cancer cell lines. Up to now, there have been no attempts to analyze, in a comprehensive manner, low molecular weight constituent elements contained in the culture supernatants derived from cultured cells. The reason for using these materials as the subject, instead of clinical samples, is that serum contains a large quantity of proteins such as serum albumin and immunoglobulins, which can hinder the detection of molecules contained in trace amounts. Sera used in cell cultures pose similar problems. Secondly, the maintenance of cell lines in vitro does not necessarily mean that the cell lines have lost the original traits of tumors. This concept has been supported by the fact that cultured cell lines also produce currently-established tumor markers frequently [Matsumoto et al., J. Cancer Rec. 82:820-828 (1991), Iwamura et al., Jpn. J. Cancer Res. 78:54-62 (1987), Sujino et al., Hum. Cell 1:250-255 (1988)].

Thus, it is likely that the profiling of low molecular weight constituent elements of culture supernatants of cell lines by MALDI or SELDI may represent a practical approach in finding secretory peptides. Specifically, since SELDI obviates the necessity of sample preparation, it will be advantageous in the approach of searching for biomarkers based on cell lines. Using a protocol optimized according to the present invention, the present inventors were able to perform differential profiling, for the first time, using a few μl of the stock solution in a one-hour experiment. This strategy will further facilitate the discovery of target peptides.

Furthermore, in order to detect trace amounts of low molecular weight peptides that could not be detected in a few μl of the stock solution as mentioned above, a sample preparation method of concentrating peptides without increasing background was established. In order to concentrate trace amounts of peptides in a test sample, a micro column equipped with a strong cation exchange membrane was used to make the sample acid with acetic acid, followed by centrifugation to recover the supernatant. The supernatant was applied to the micro column so as to be bound to the ion exchange membrane.

After washing, an alkaline volatile eluting solution (ammonia, water, acetonitrile=1:4:5 v/v) was added to the bound analyte, which is then centrifuged and recovered. By repeating this step, the recovery rate can be increased. The eluates are combined, and concentrated under reduced pressure. By analyzing this prepared solution on a SELDI protein chip, the analysis of peptides became possible, which analysis was no possible for the stock solution. Furthermore, the use of this preparation method enabled analysis by MALDI.

A point to be considered here is that polypeptides secreted from the cell into the culture medium account for as little as 0.01% in terms of the total molar concentration and even less for peptide fractions. Inorganic salts account for 85% of the total. Though the surface-enhanced laser desorption ionization (SELDI) protein chip makes it possible to capture the analyte on the chip, the use of sample preparation permits the washing of components, other than analyte, such as inorganic salts, and thereby the concentration of polypeptides present in the culture supernatant.

After preparing the chip, analysis is performed in the range of 2000 to 15000 Da using a SELDI mass spectrometer. Instead of spots on the stained gel, constituent elements are presented as molecular mass on mass spectra. As far as the present inventors know, the present invention is the first example in which a culture supernatant was used in a protemic peptide analysis. It should be specifically noted that it only requires a few μl of the culture supernatant to obtain a mass spectrum representing an expression pattern unique to each cell line.

If peptides are subjected to differential display for the purpose of searching tumor markers, procedures that can be easily performed are preferred since a multitude of samples must be processed. Furthermore, in addition to concentrating peptides present in the culture supernatant, inorganic salts must be removed at the same time. In this regard, it appears that the SELDI H4 chip captures analytes as reverse phase chromatography does, and enables the removal of contaminants and concentration to be performed on the chip. In accordance with the present invention, by using only a few μl of the culture supernatant of serum-free stock solution, the expression pattern of low molecular weight constituent elements can be identified.

Furthermore, according to the present invention, a strategy of detecting peptides occurring in smaller amounts was established in order to increase chances of finding target peptides. When mass spectra are compared before and after this one-step preparation, it is estimated that peptides occurring at amounts of 1-10 pmol/ml in the culture supernatant of the stock solution have been efficiently concentrated by this method. However, not all peptides have been ionized to the same degree and detected.

In standard ion exchange chromatography, bound substances are eluted by increasing the salt concentration. However, since inorganic salts are more easily ionized than peptides [Carr et. al., Current Protocols in Molecular Biology, John Wiley & Sons, Inc., New York Units 10. 21 (1997)], the detection of peptides is hindered. Thus, in accordance with the present invention, instead of using the method of increasing salt concentrations in one-step preparation, acetonitrile and ammonia are used as eluting reagents to recover peptides captured on the membrane. These reagents are volatile, and hence the eluted substances can be easily concentrated without concentrating inorganic salts.

This method of sample preparation also becomes suitable for other analytical methods by diluting samples in appropriate buffers. Until now, there have been no reports on the analysis of peptides in culture supernatants, nor have there been reports on proteomic analysis for any of cultured cells and clinical samples with regard to pancreatic cancer. Data according to the present invention indicate that culture supernatant of pancreatic cancer cells contain a large quantity of peptides secreted from the cell.

In accordance with the present invention, furthermore, a peptide with a molecular weight of about 3335, that is specifically secreted from subcultured cells derived from pancreatic cancer, was discovered by using the above method of concentrating low molecular weight peptides and the hydrophobic protein chip mass spectrometry to compare peptides secreted from subcultured cells derived from various pancreatic cancers and from non-pancreatic cancers. Peptides that are specifically secreted from cells derived from pancreatic cancer are not limited to the molecular weight, and by increasing subcultured cells to be compared it is possible to discover peptides with other molecular weights.

A peptide with a molecular weight of about 3335, that is specifically secreted from cells derived from pancreatic cancer, can be isolated and purified from the culture supernatant of pancreatic cancer-derived cells. Purification to the desired purity can be carried out by combining various known methods for isolation and purification. Purification methods that can be used include, for example, chromatography such as cation exchange chromatography, anion exchange chromatography, gel filtration chromatography, hydrophobic chromatography, isoelectric chromatography, immunoaffinity chromatography, chelate affinity chromatography and reverse phase chromatography, separatory precipitation such as salting out and the like. Other methods can also be used.

After obtaining said peptide at a sufficient purity and a sufficient amount, it can be subjected to protein sequencing to determine the amino acid sequence from the N-terminal. The amino acid sequence in the vicinity of the N-terminal can be determined by first digesting said peptide with a suitable protease etc., purifying degradation products, i.e. partial peptides, by a purification method such as reverse phase chromatography, determining the amino acid sequence from the N-terminal in a similar manner, and then combining the sequences to determine the entire amino acid sequence.

Thus, the entire amino acid sequence can be determined in this manner, but it is not always necessary. It is also possible to use a general method to clone DNA encoding the peptide from a partial amino acid sequence and to determine the base sequence, based on which the amino acid sequence of said peptide can be determined.

More recently, furthermore, it has also become possible to determine the sequence of amino acids from trace amounts of samples. For example, using tandem mass spectrometry, the amino acid sequence can be determined by a combined use of the mass tag method and the de novo sequencing method. The amino acid sequence of the peptide with a molecular weight of about 3335 of the present invention was also determined in such a method, and it was found to represent a 29-amino acid residue at the C-terminal end of the DMBT1 gene which is thought to be a potential tumor suppressor gene.

DMBT1 (deleted in malignant brain tumors 1) belongs to the scavenger receptor cysteine-rich (SRCR) superfamily, and has been reported to be a potential tumor suppressor gene for brain tumor, lung cancer etc. (Cancer Res. 2000, 60:1704-1710). There are no reports, however, that indicate the relationship between pancreatic cancer and the DMBT1 gene, nor are reports that demonstrate that 29-amino acid residue at the C-terminal end of a peptide encoded by the DMBT1 gene is released into the supernatant of subcultured cells derived from pancreatic cancer and, in this regard, the present invention is the first discovery.

With regard to this peptide encoded by the DMBT1 gene, the 29-amino acid residue at the C-terminal end thereof has been specifically secreted from subcultured cells derived from pancreatic cancer, indicating a high possibility that it could be detected in samples from patients with pancreatic cancer. This shows that the 29-amino acid residue is useful for early discovery of pancreatic cancer and as a marker for treatment thereof. Furthermore, it is believed that a polypeptide that contains part or all of the 29-amino acid residue could similarly be a marker for pancreatic cancer. Part of the 29-amino acid residue as used herein means 15 or more contiguous amino acids, preferably 20 or more contiguous amino acids, and more preferably 25 or more contiguous amino acids.

The same holds true for 20 amino acids at the C-terminal end of the peptide encoded by the integral membrane protein 2B gene described below as for the 29 amino acids of the DMBT1 gene.

The peptide of the present invention comprises an amino acid sequence substantially identical to the determined amino acids. "Substantially identical" as used herein means that it is completely identical or it has been modified by one or several amino acids but still can serve as a diagnostic marker for pancreatic cancer. "Modification" as used herein means that amino acids have been altered by amino acid deletion or addition, or replacement with another amino acid, or by combinations thereof. Sugar chains and fatty acids may also be included.

"Several" as used herein means, for example, not greater than about 20% relative the total number of amino acids, preferably not greater than 10%, for example not greater than six, and preferably not greater than three amino acids. Thus, in the substantially identical amino acid sequences according to the present invention, 1-6, preferably 1-3 amino acids, may be added, deleted or replaced, and amino acid sequences that could serve as a pancreatic cancer marker may also be included.

The present invention also includes peptide fragments having various amino acid sequences mentioned above. These fragments are useful as an immunogen for antibody production regardless of their usefulness as diagnostic markers for pancreatic cancer. "Fragments" as used herein means sequences of 15 or more contiguous amino acids, preferably sequences of 20 or more contiguous amino acids, and more preferably sequences of 25 or more contiguous amino acids.

The present invention also encompasses fusion peptides of the above peptides or fragments thereof and other peptides. Peptides that could become partners to constitute a fusion peptide include any peptides such as glutathione S-transferase, superoxide dismutase, and lacZ. Such fusion peptides are useful in efficiently expressing the peptide of the present invention or fragments thereof by a recombinant technology.

The present invention relates to derivatives of the above peptides and fragments thereof.

The peptides of the present invention and fragments thereof can be chemically synthesized according to standard methods. Those methods include those described in Janis D. Young, Solid Phase Peptide Synthesis (Pierce Chemical Co., Rockford, Ill., 1984); in M. Bondanszky and A. Bondanszky, The Practice of Peptide Synthesis (Springer-Verlag, New York, 1984), and in M. Bondanszky, The Principles of Peptide Synthesis (Springer-Verlag, New York, 1984).

Said prepared peptides or fragments thereof can be isolated and purified from reaction mixtures using a general method for peptide separation such as extraction, precipitation, electrophoresis and various types of chromatography.

Also, by gene engineering technology, the peptides of the present invention, their fragments or fusion peptides thereof can be produced. In such methods, a host transformed with an expression vector comprising DNA encoding the desired peptide or polypeptide is cultured, and the desired peptide or polypeptide may be harvested from said culture. For this purpose, the host may be eukaryotic or prokaryotic cells. Prokaryotic cells are, for example, bacteria, and they may be Gram positive or Gram negative.

The peptides of the present invention or fragments thereof may be obtained in various purities depending on the desired uses. They may be purified by immunoaffinity chromatography with antibody described herein using a peptide purification technology disclosed herein. The outline of this immunoaffinity chromatography has been described in this specification.

The peptide of the present invention or DNA encoding it has a variety of applications. Thus, in addition to being used for the production of the peptide encoded thereby, the DNA is particularly useful in detecting or identifying genes encoding related or homologous peptides, genes encoding subtypes of said peptide, and genes encoding said peptide from different species.

The present invention also relates to the use of said peptide, fragments thereof, peptides and fusion products thereof in various assay systems and diagnostic reagents for detecting or quantitating the presence of said peptide.

The peptide of the present invention or fragments thereof can also be used as standards in the above assay system.

The peptide of the present invention or fragments thereof can also be used as an immunogen for the production of antiserum or antibody specific for said peptide or fragments thereof. The peptide purified may be used to screen monoclonal antibodies prepared by immunization of crude-purified peptide preparations. Furthermore, said peptide or fragments thereof can also be used as an immunogen for the production of antibody of the present invention.

The present invention provides a probe that has an affinity with, and binds to, said peptide. "Probe" as used herein means a substance that binds to said peptide. Thus, using this binding of the probe to said peptide, the peptide in test samples can be detected. As probes, there can be mentioned receptors, ligands, DNA, peptides, aptamers, antibodies etc. having an affinity with said peptide. Detection may be effected by capturing a ligand in test samples with these probes. Detection may also be effected by labelling these probes with an enzyme etc. The probe is explained below with antibody as a representative example.

The present invention provides antibody having an affinity with said peptide. For example, the present invention relates to an antibody or fragments thereof having an affinity with or raised against a peptide having a molecular weight of about 3335. The antibody can be generated against said peptide and a fragment thereof in naturally occurring form and in recombinant form.

Antibody against the fragment of the peptide of the present invention can be prepared by immunizing an animal with a conjugate of an immunogenic peptide and said fragment. Monoclonal antibody may be prepared from cells that secrete the desired antibody. These antibodies can be screened for binding to said peptide.

The peptide of the present invention and a fragment thereof may be fused or covalently bound to a polypeptide to be used as an immunogen, and then immunized. Said peptide and a fragment thereof may be fused or covalently bound to various immunogens such as keyhole limpet hemocyanin, bovine serum albumin and tetanus toxoid, and then immunized. Animals to be immunized may be any species as long as they can be immunized to obtain the desired antibody including cattle, horses, goats, sheep, rabbits, chickens, guinea pigs, rats, mice and the like.

For explanation on methods of preparing polyclonal antiserum, see for example Microbiology, Hoeber Medical Division (Harper and Row, 1969), Landsteiner, Specificity of Serological Reactions (Dover Publications, New York, 1962), and Williams et al., Methods in Immunology and Immunochemistry, Volume 1 (Academic Press, New York, 1967) (all of them are incorporated herein by reference). Typical methods encompass hyperimmunization of animals with antigen.

The polyclonal antibody of the present invention can be obtained according to a standard method. Animals such as horses, goats, sheep, rabbits, chickens, guinea pigs etc. are regularly immunized with the above antigen peptide alone or in an admixture with an adjuvant. Preferably after three immunizations, the blood, eggs etc. are collected from the immunized animals and then polyclonal antibody can be recovered.

The present invention also provides a monoclonal antibody that has a binding property with said peptide. The present invention further provides a hybridoma that produces the above monoclonal antibody.

In many cases, it is desired to prepare monoclonal antibody from rodents such as mice and rats, primates, humans etc. Explanations on the technique for preparing such monoclonal antibody can be found in Stites et al., Basic and Clinical Immunology (Lang Medical Publications, Los Altos, Calif. Vol. 4) and the cited references therein, and specifically Kohler and Milstein, Nature 256:495-497 (1995) (discussion on a method of preparing monoclonal antibody).

In brief, mice, rats etc. are regularly immunized with the above antigen alone or in an admixture with an adjuvant. Preferably after 3 or more immunizations, the spleen or a lymph node is extracted and the B cells are subjected to cell fusion with suitable myeloma cells. The fused cells are "hybridoma" that can be cultured in vitro. The hybridoma cells thus obtained are cultured in a suitable culture liquid such as the HAT-RPMI1640 medium containing 10% bovine fetal serum.

By detecting the antibody produced using RIA, ELISA or the like, hybridoma cell lines are selected that produce the antibody that specifically react to said peptide, and are cloned. Each clone secretes one antibody species against the immunogen. Individual antibody species obtained are products of single B cells from the immunized animal generated in response to a specific site (epitope) recognized on the immunogenic substance.

Monoclonal antibody that reacts with the peptide of the present invention may be obtained by transplanting hybridoma cells into the abdominal cavity of mice or rats and then recovering the antibody from the ascites obtained. It can also be recovered from the culture supernatant of the hybridoma cells.

The recovered monoclonal antibody or polyclonal antibody may be separated and purified by a known method such as ammonium sulfate precipitation and chromatography.

The antibody of the present invention may also be used for affinity chromatography. This affinity chromatography can be used for the purification of said peptide. By preparing a column in which antibody has been bound to a solid support such as particles (e.g. agarose, Sepharose) or a similar substance, a sample containing said peptide is passed through the column, and then running a weak denaturing agent, the purified peptide can be eluted.

The present invention also provides a method of measuring said peptide comprising said antibody, and a method of detecting and measuring a fragment thereof.

The detection system and the measurement system of said peptide may be homogeneous (no separation step is included in between a releasing reagent and said peptide-antibody complex) or heterogeneous (a separation step is included).

The detection system and the measurement system of said peptide of the present invention typically comprise a labelled antibody having a binding affinity for said peptide, a source (naturally occurring or recombinant) of said peptide, and a means to separate the conjugate from the labelled free compound, for example an antibody having a binding affinity for said peptide immobilized for fixing said antibody.

In such a measurement system, by labelling directly or indirectly the antibody or said peptide and a fragment thereof by non-covalent or covalent bonding, detectable signals can be obtained directly or indirectly. Direct labelling includes, for example, radioactive labelling, for example $^{125}$I, enzyme (U.S. Pat. No. 3,645,090), for example peroxidase or alkaline phosphatase, and a fluorescent label (U.S. Pat. No. 3,940, 475), and the like. It further encompasses, for example, biotinylation and binding to biotin of avidin or streptoavidin labelled with one of the above labells. For example, non-labelled antibody can be used by using a labelled second antibody that labels the antibody.

The antibody obtained to said peptide can be used to construct known immunoassays such as radioimmunoassay (RIA), enzymeimmunoassay (EIA), and fluorescent immunoassay (FIA), which are used to detect or determine said peptide or a fragment thereof.

As an example of a known immunoassay, there can be conceived the use of the so-called competitive immunoassay. For example, the sample is mixed with a fixed amount of the peptide labelled with a radioisotope etc., to which antibody to said peptide is further mixed so as to allow the reaction of said peptide in the sample with the labelled peptide.

As the peptide in the sample competes with the labelled peptide for binding to antibody to said peptide, reaction with the labelled peptide decreases as much as said peptide is present in the sample. After the reaction, by allowing anti-peptide antibody to be bound to the solid carrier beforehand, or allowing anti-peptide antibody to react to anti-immunoglobulin antibody or Protein A, the bound and unbound labelled peptide can be separated. Using a commonly employed method, the unbound fraction is removed, and the bound label, such as a radioisotope, is detected so as to enable the measurement of said peptide.

As another example of a known immunoassay, there can be mentioned a use of the so-called double antibody sandwich system. For example, an anti-peptide antibody is bound to a solid carrier commonly used in immunoassay such as a microtiter plate, beads, a nitrocellulose membrane, and a nylon membrane, which is brought into contact with the test sample so as to effect the reaction of said peptide in the sample with an anti-peptide antibody on the solid carrier. The unbound fraction is washed away by a commonly employed method, and the carrier is brought into contact with an anti-peptide antibody labelled with a radioisotope, an enzyme, a fluorescent substance, biotin and the like so as to allow the reaction of the anti-peptide antibody with the bound peptide.

By washing away the unbound fraction by a commonly employed method and detecting the labelled radioisotope, enzyme, fluorescent substance, biotin and the like, said peptide can be determined. As the anti-peptide antibody and the labelled anti-peptide antibody for use in this assay system, any of monoclonal antibody, polyclonal antibody or a combination thereof can be used. What is important here is the combination of antibody so as to permit the binding of a complex of the antibody that binds to the carrier and said peptide to the labelled antibody, and such a combination of antibodies can be selected by setting up the above-mentioned system and then applied to the system.

Furthermore, using immunohistochemistry, said peptide or a fragment thereof in the tissue can be detected and, besides, the manner of localization in the tissue and the cell can be known. As examples of antibody labelling for use in immunohistochemistry, there can be mentioned a fluorescent dye and an enzyme for use in an optical microscope, and ferritin and colloidal gold for use in an electron microscope. For immunohistochemistry, typically tissue sections or cells are fixed by a suitable fixing agent such as alcohol, acetone, and paraformaldehyde, to which is reacted an anti-peptide antibody. After washing, it is used as it is in the case of direct labelling, and further reacted with a labelled substance, in the case of indirect labelling, and washed, and then detected by a fluorescent microscope in the case of fluorescent labelling, by an optical microscope after reacting with a suitable substrate in the case of enzyme labelling, and by an electron microscope in the case of metal-particle labelling.

These immunoassays have been intensively discussed in the literature.

The antibody of the present invention is also useful for diagnosis.

Results obtained from the above immunohistochemistry and immunoassay demonstrate how the peptide is present and localized in the cell and tissues. This not only gives insight into the physiological role of said peptide but reveals its relation to various diseases. Its relation to a disease suggests the usefulness as a diagnostic reagent for the disease.

The peptide of the present invention with, for example, a molecular weight of about 3335 is a peptide that is specifically expressed and secreted from subcultured cells derived from pancreatic cancer. Thus, if the peptide is an antigen present in a pancreatic cancer-specific manner, it could be useful as a cancer marker for diagnosis.

Thus, by using the above peptide or a fragment thereof as a diagnostic reagent, useful information as a pancreatic cancer marker could be obtained on screening of patients at physical checkup etc., identification of properties of the disease, therapeutic monitoring during therapy, and the like.

Analytes include body fluids such as blood and saliva, excrements such as urine and feces, harvested tissues and cells, and the like.

EXAMPLES

The present invention will now be explained more specifically with reference to specific examples.

Example 1

Preparation of a Serum-free Culture Supernatant

A cell line was cultured to confluence in a RPMI1640 medium containing 10% fetal bovine serum (Life Technologies). After aspirating the medium, it was washed three times in 10 ml each of a serum-free medium, and further cultured at 37° C. for 1 hour. After two more washings, 3 ml of the medium per 10 cm culture dish was added and cultured for 48 hours.

After removing the cells in a centrifuge, the culture supernatant was transferred to a polypropylene tube and stored at 4° C. until analysis. The protein concentration was determined using the Protein Assay kit (Bio-Rad) with immunoglobulin as a standard. As a control, a medium containing 10% serum was added to an unused dish and cultured for 72 hours, which was then washed as described above and used. The medium obtained is termed a "cell-free" culture supernatant. For all cell lines, trypan blue dye exclusion test was performed, confirming that 95% or more cells survived for 48 hours.

Example 2

Optimization of SELDI Analysis for Profiling Low Molecular Weight Proteins

Mass was determined using Ciphergen SELDI Protein Biology System 2 (Ciphergen Biosystems, Inc., CA) as a mean of 110 laser shots. For spectral analysis, monovalent and divalent molecular ions of bovine insulin were used to carry out external calibration (m/z 5734.56 and 2867.78). Values of m/z when referred to in the text were rounded to three-place or four-place significant figures. Precision of mass was better than 1000 ppm (0.1%) in the analytical range.

In order to analyze low molecular weight proteins, the H4 protein chip array having a chemical surface that captures protein with hydrophobic interaction was used. The experimental conditions for sample binding and matrix cocrystals were optimized to obtain spectra. As the application of mass spectrometry in protein profiling of biological materials is at a development stage and thus there are no established protocols, the optimization thereof is very important. In a similar manner to reverse phase column, the H4 chip was first activated with 1 μl of 100% acetonitrile (ACN), and then treated with water-ACN (90:10, v/v), water-ACN (50:50, v/v), or 0.5% TFA-containing water-ACN (50:50, v/v).

Figure 2:
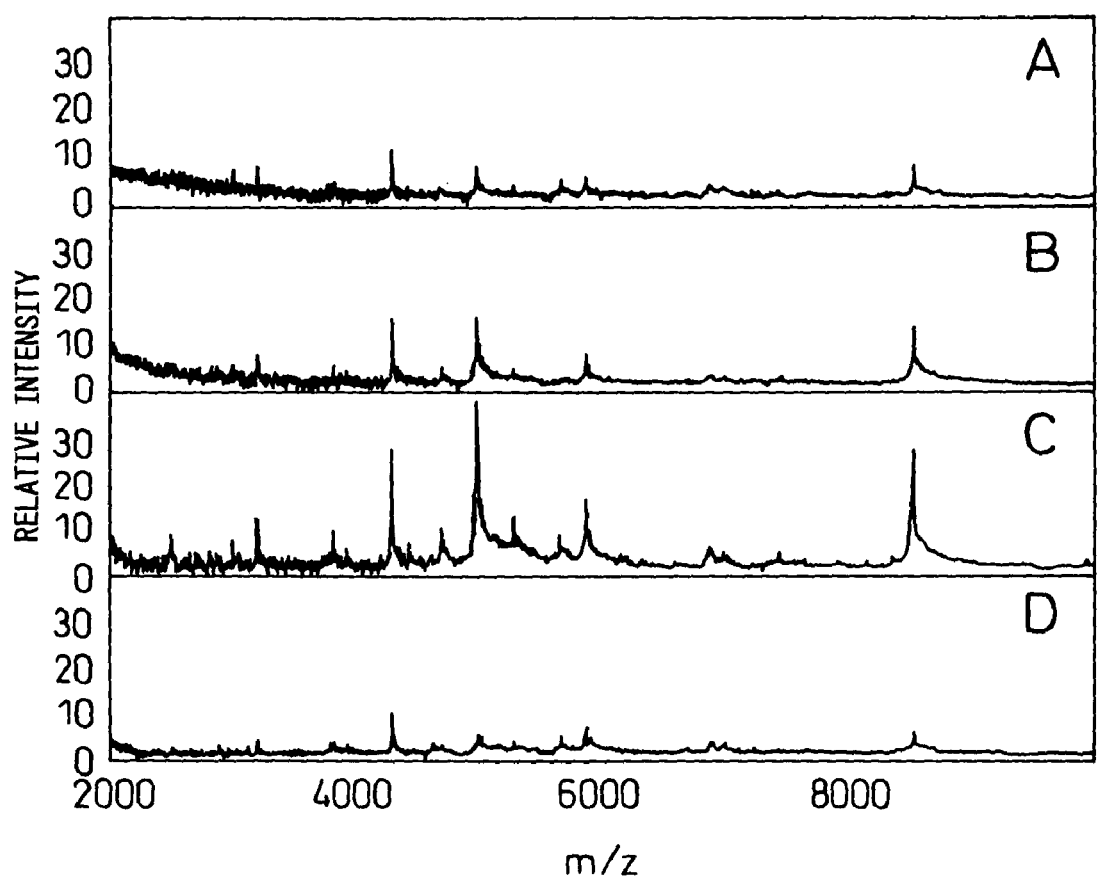
FIG. 2 shows a comparison of SELDI mass spectra obtained by three different pretreatments. Each of the spots was equilibrated using (A) H2O-ACN (90:10, v/v), (B) H2O-ACN (50:50, v/v), or (C) 0.5% TFA-ACN (50:50, v/v). (D) underwent a pretreatment similar to (C), but a saturated CHCA was used as the matrix.

Furthermore, the MKN-1 cell-conditioned medium (200 ng protein per spot) was added as a sample, and after allowing to stand for 10 minutes the chip surface was washed. To the spots, a 5-fold diluted solution of saturated α-cyano-4-hydroxy cinnamic acid (CHCA) was added. This reagent is a matrix commonly used in mass analysis of polypeptides. The spots treated with 0.5% TFA-containing water-ACN (50:50, v/v) gave the best spectrum (C in FIG. 2).

Instead of CHCA, 3,5-dimethoxy-4-hydroxy cinnamic acid (SPA) or 2,5-dihydroxy benzoic acid (DHB) which is also used in mass analysis of polypeptides was also examined, but satisfactory results could not be obtained. Higher signal intensity was obtained when the concentration of CHCA was a 5-fold diluted solution rather than the saturated solution (D in FIG. 2). Thus, the treatment of chip was optimized in a method shown in FIG. 1. Similar results were obtained for the other two cell lines.

Example 3

Comparison of Tricine Electrophoresis and SELDI Analysis

Using the protocol in Example 2, low molecular weight molecules were analyzed for five cell lines using 5 μl each. Protein concentration varied depending on the cell line (0.05-0.8 mg/ml), being equivalent to 250 ng to 2 μg analyzed per spot as the amount of total protein. Data were compared with those obtained by tricine SDS-PAGE that has been established as a technique for protein separation [Schagger et al., Anal. Biochem. 166:368-379 (1987)]. In order to perform tricine SDS polyacrylamide gel electrophoresis, 100 μl of the culture supernatant was concentrated to 20 μl, which was then dissolved in the sample buffer.

Figure 3:
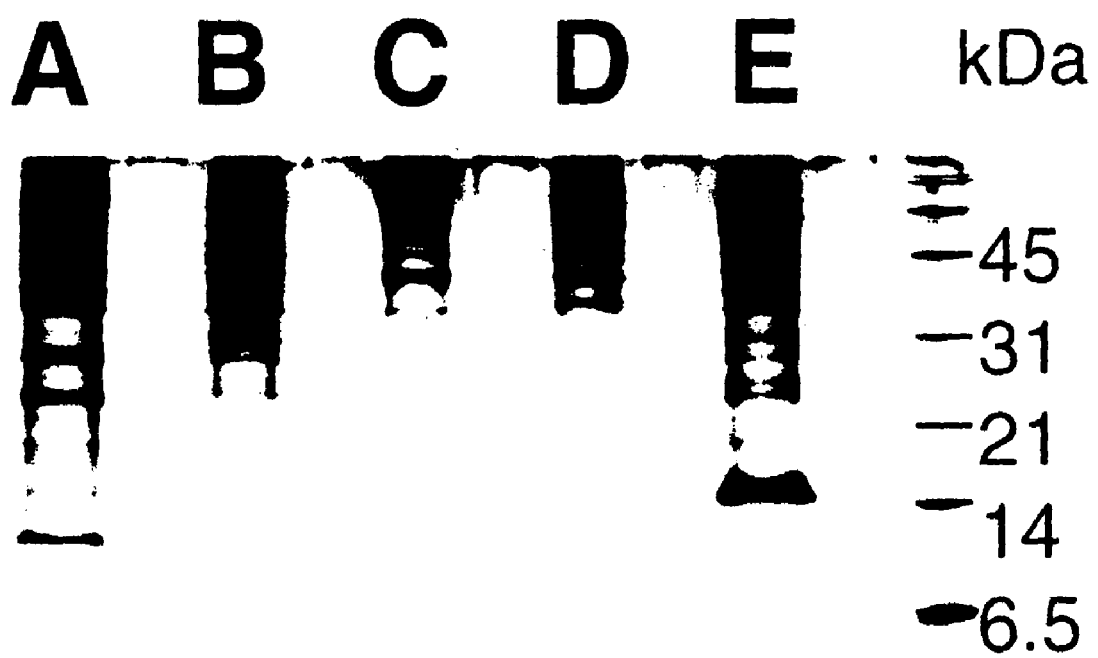
FIG. 3 shows the result of Tricine PAGE analysis for comparison with the SELDI analysis. This is a photograph of the Tricine SDS-PAGE gel after silver staining.
Figure 4:
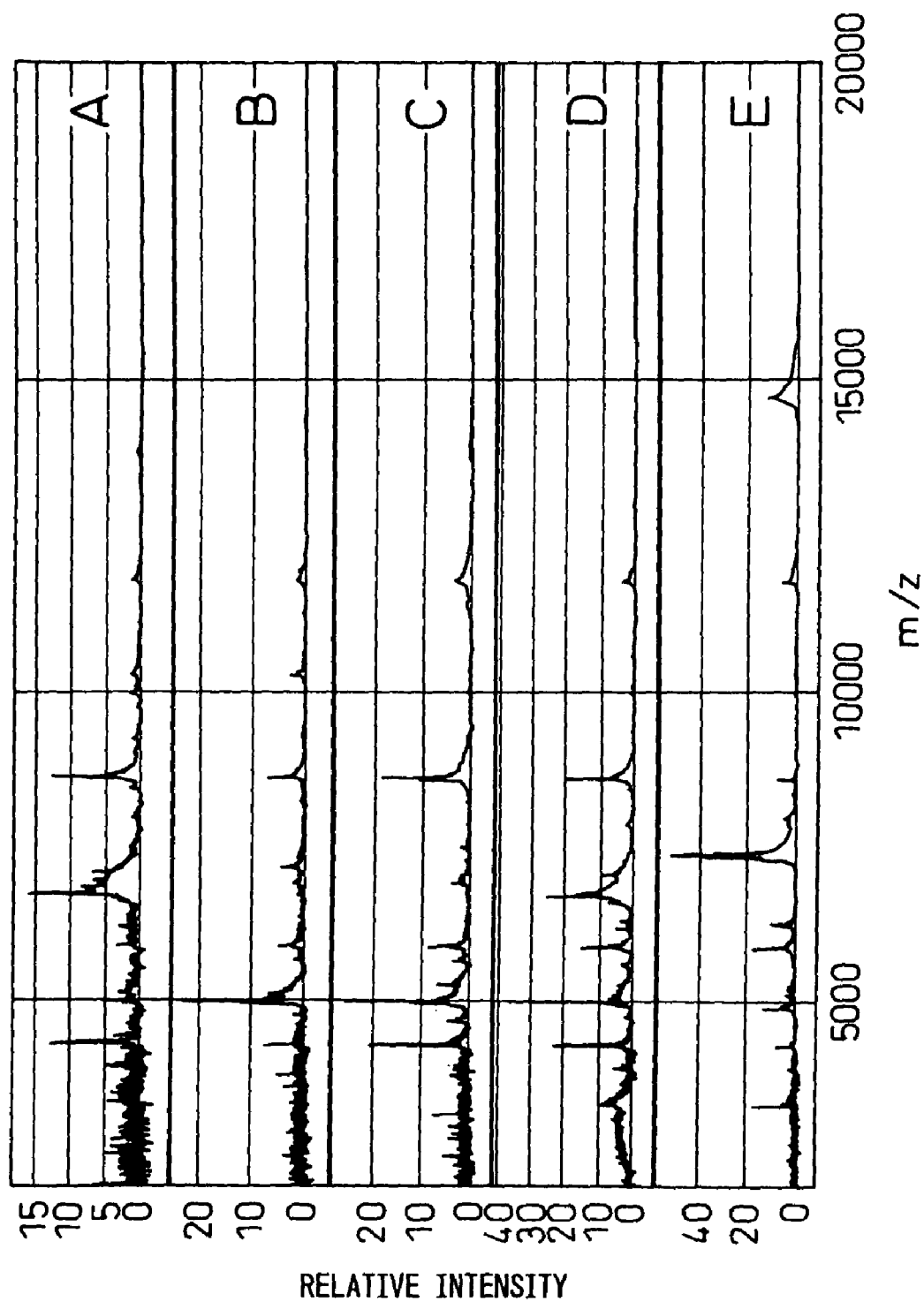
FIG. 4 shows the result of the SELDI analysis for comparison with the Tricine PAGE analysis, and is mass spectra of m/z 2,000-20,000. A represents the result of MDA-MB-361, B represents the result of MDA-MB-231, C represents the result of MKN-1, D represents the result of T-47D, and E represents the result of Capan-1.

The gel composition used was 16.5% T-3% C. The bands were visualized by silver staining. Even when 100 μl of sample was used, electrophoresis detected only a small number of bands in the range of molecular weight 20000 or lower (FIG. 3). In the SELDI analysis, on the other hand, many signals were found in the range of m/z 20000 or lower at $\frac{1}{20}$ the amount of the sample used in the electrophoresis (FIG. 4). It should be note herein that spectral peaks do not always indicate the presence of as many molecular species. It is because proteins having a high relative content may produce multi-valent molecule ions [Carr et al., Current Protocols in Molecular Biology, John Wiley & Sons, Inc., New York Units 10. 21 (1997)].

Figure 5:
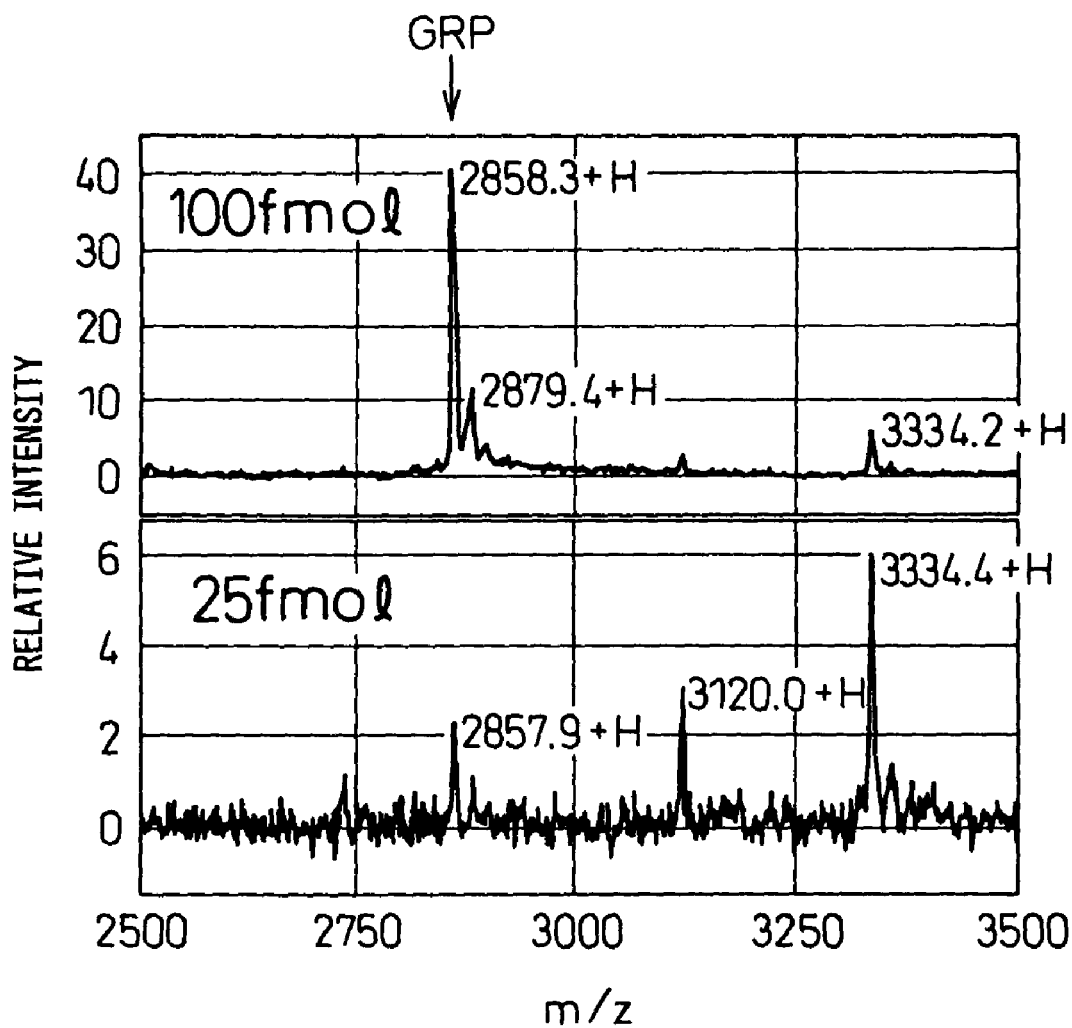
FIG. 5 shows the detection of GRP (25-100 fmol/spot) applied onto 1 µl of a Capan-1 culture supernatant.

Despite such characteristics, SELDI appears to detect more peaks in the low molecular weight range. Using GRP (molecular weight 2859.4) a given amount of which was added to 1 μl of the culture supernatant of CAPAN-1, sensitivity was evaluated. At a signal-to-noise ratio of 3, 25 fmol of GRP was easily detected (FIG. 5). These findings suggest that SELDI is superior in detecting low molecular weight proteins.

Another characteristics of SELDI is time required for analysis. Tricine electrophoresis takes a whole day for analysis including sample concentration and detection, while in SELDI H4 protein chip, the experiment is complete in one hour because the step of sample preparation is not necessary. In standard MALDI, a procedure such as desalting is required prior to analysis, but desalting can be performed in one minute on the SELDI chip. In desalting with Millipore's ZipTip or Waters' Sep-Pak cartridge, it was difficult to recover a few μl of sample in a reproducible manner. Another advantage of H4 is the small volume of reagents used, which is about 10 μl or less per spot.

Example 4

One-step Sample Preparation

In order to realize the detection of even smaller amounts of low molecular weight peptides by protein chip mass spectrometry, concentration of low molecular weight peptides was examined. Prior to sample addition, the Microcon-SCX (Millipore), a microcolumn equipped with a strong cation ion exchange membrane, was sequentially washed in 500 μl of methanol and an equal amount of water. The sample (750 μl) was diluted in an equal amount of 1% acetic acid, and centrifuged at 14000 g for 5 minutes.

The supernatant was added to the microcolumn after conditioning and then allowed to bind to the ion exchange membrane. It was further washed in 500 μl of 0.1% trifluoroacetic acid (TFA). The bound analyte was recovered by adding 50 μl of the eluting solution (ammonia, water, acetonitrile=1:4:5 v/v), and centrifuging at 14000 g for 30 seconds. This step was repeated. The eluates were combined, and concentrated to 30 μl under reduced pressure. Three μl per spot was analyzed on the SELDI protein chip according to Example 5.

Example 5

SELDI Protein Chip Analysis after One-step Sample Preparation

The sample prepared in Example 4 was measured on the C16 reverse phase H4 Protein chip Array (Ciphergen Biosystems, Inc.) using a method optimized in Example 1.

Data were analyzed using PEAKS, a SELDI software.

Figure 6:
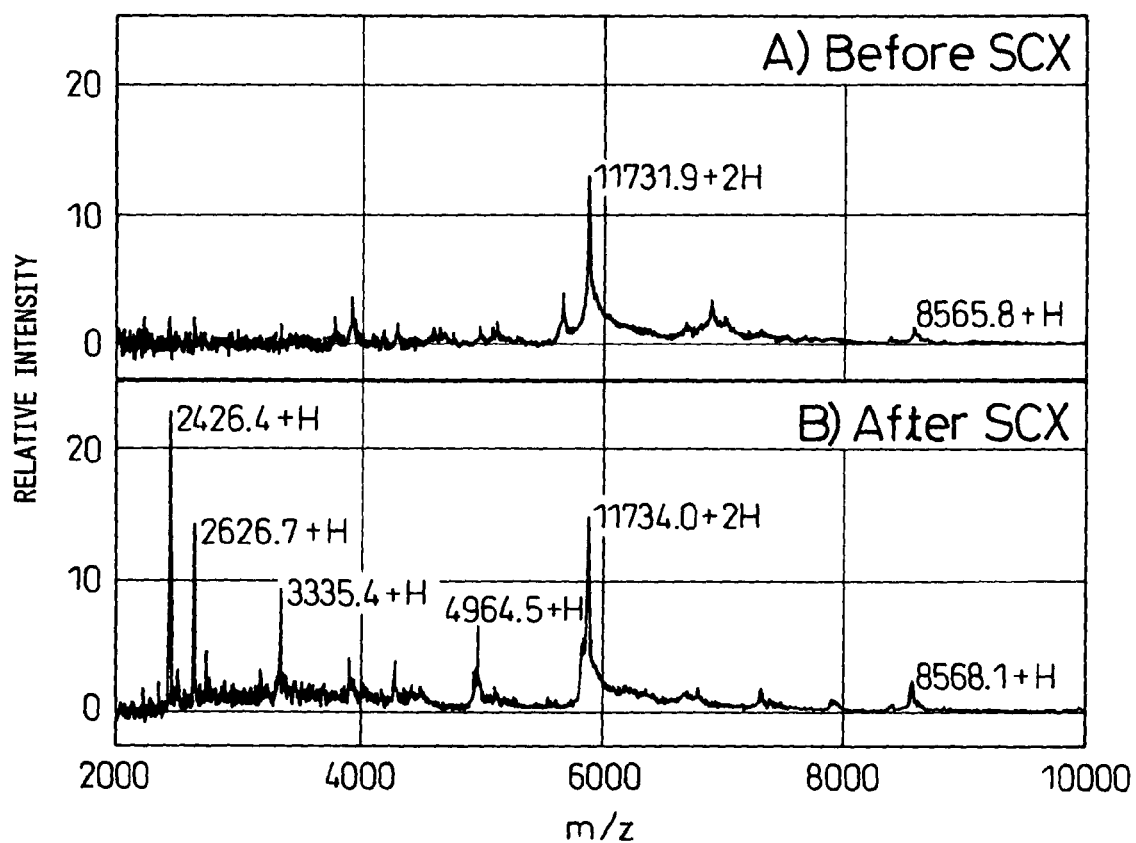
FIG. 6 is a chart showing the result of enhancement in signal detection by sample preparation using a strong cation ion exchange membrane. In the figure, A represents the result of a untreated culture supernatant (2.5 µl), and B represents the result of a SCX-treated sample (3 µl).

Total protein concentration varied with each cell line, being in the range of 0.05 mg/ml to 0.9 mg/ml. When 2.5 μl of the culture supernatant of the stock was used, peaks were hardly seen on the H4 chip that captures the analyte by hydrophobic interaction at m/z 5000 or lower (A in FIG. 6). It appeared that in order to increase the chances of finding trace molecules, it was only necessary to repeatedly add the analyte to the chip.

However, even by using the H4 chip, sample amounts greater than 5 μl have also brought a large amount of salts into the chip, thus exceeding the analytical performance. In fact, when the culture supernatant of the stock solution, at amounts greater than 10 μl, is added, salts are formed on the chip, resulting in reduced performance of mass spectrometry in terms of the number and intensity of signal detected. In order to concentrate peptide fractions, samples were made acid by adding an equal amount of 1% acetic acid, and were bound to a strong cation ion exchange membrane in order to capture amino acids and peptides.

Substances that bound were eluted under an alkaline condition as described in Example 4, and were further concentrated under reduced pressure. Analysis of the concentrate revealed a plurality of peaks that could not be found for the stock solution at m/z 5000 or lower (B of FIG. 6). Peaks having m/z greater than 5000 could not be concentrated.

Example 6

Protein Profiling on the Reverse Phase H4 Protein Chip

Figure 7:
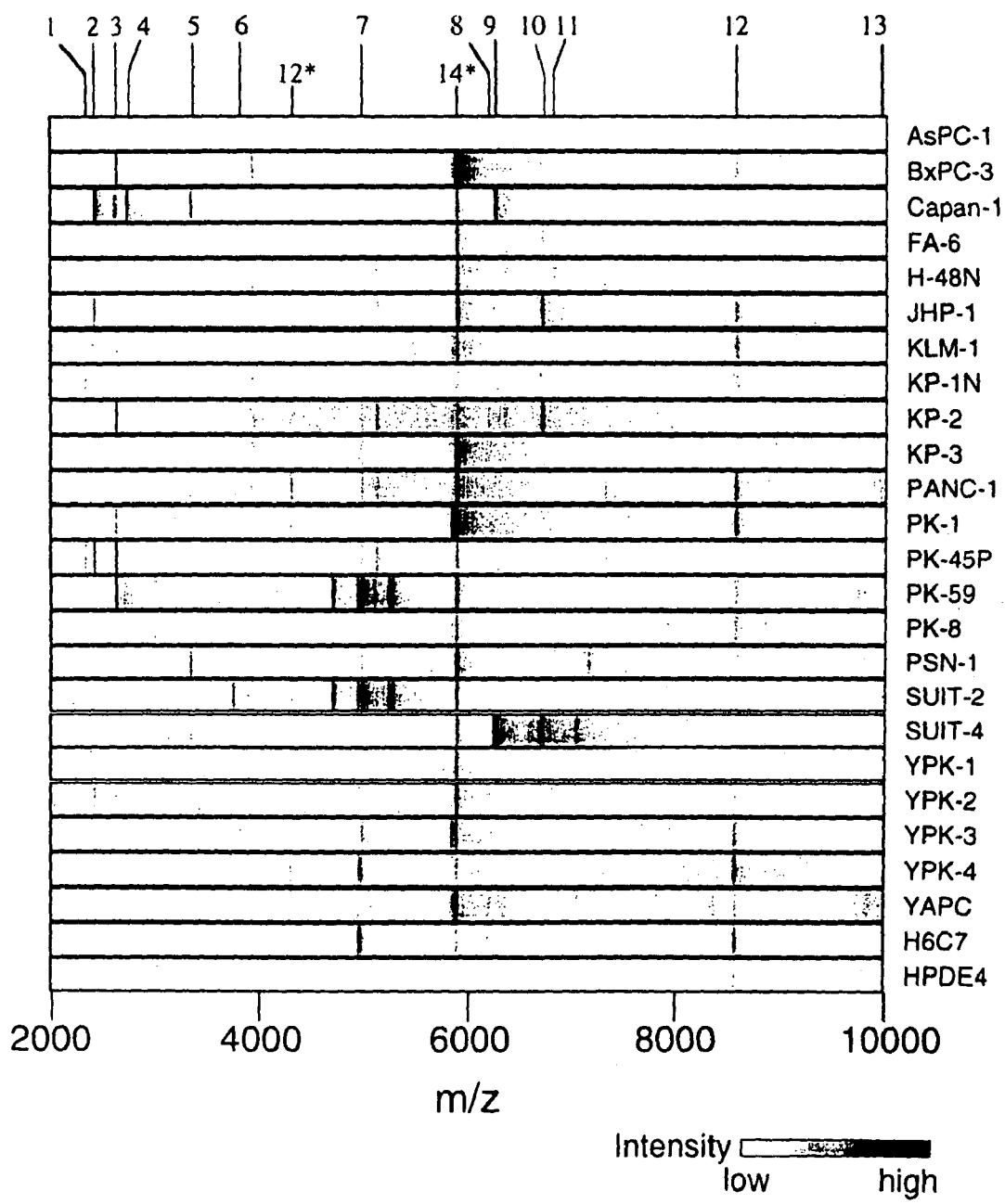
FIG. 7 shows mass spectra obtained from 25 cultured cells. Each culture medium was treated as described in Examples and 3 µl was analyzed by the H4 chip. An asterisk indicates a divalent ion.

A culture supernatant was prepared from each of 23 pancreatic cancer cell lines using the method described in Example 4, and analyzed with the H4 chip. As a control, the culture medium of the H6C7 cells and HPDE4 cells [Am. J. Pathol. 157 82000) 1623-1631] established from normal pancreatic duct cells having the E6E7 gene of human papilloma virus 16 introduced therein was examined. Though immortalized, these cells are more similar to the normal pancreatic duct cells than to malignant duct cells, thereby having no tumorigenicity in nude mice [Am. J. Pathol. 157 (2000) 1623-1631]. In FIG. 7, mass spectra of these 25 lines were represented in either white or black in a signal-dependent manner.

As no signals were detected from the media that were brought into contact with the culture dish, most signals are believed to be derived from cells. Signals detected at positions #12 and #14 are divalent ions at each of #12 and m/z 11734 (FIG. 7). These divalent ions are occasionally observed in matrix assisted mass spectrometry and are observed as such when the analytical software PEAKS is used. Signals were matched to differential display at a precision of 0.1%. Table 1 is a summary of the peaks detected for cancer cell lines at a signal-to-noise ratio of 2 to 5 and the expression in those 23 lines.

TABLE 1

Major low molecular weight peptides secreted from pancreatic cancer-derived subcultured cell lines

| Peak | M/z | No. of positives for pancreatic cancer-derived cell lines (n = 23) | No. of positives for normal pancreatic duct cell lines (n = 2) |
|---|---|---|---|
| 1 | 2,340 | 11 | — |
| 2 | 2,427 | 12 | — |
| 3 | 2,628 | 15 | 1 |
| 4 | 2,733 | 11 | — |
| 5 | 3,336 | 5 | — |
| 6 | 3,803 | 8 | — |
| 7 | 4,938 | 6 | 2 |
| 8 | 6,117 | 7 | 1 |
| 9 | 6,335 | 8 | — |
| 10 | 6,693 | 6 | — |
| 11 | 6,800 | 5 | — |
| 12 | 8,569 | 23 | 2 |
| 13 | 9,961 | 9 | 1 |

Peaks detected in five or more pancreatic cancer-derived cell lines are listed.

Control is normal pancreatic duct cells.

Peak #12 at m/z 8569 was observed in all cell lines. After all, 8 major signals (#1-2, #4-6, #9-11) found in cultured pancreatic cancer cell lines were not detected in the duct cell lines (Table 1). Expression in the culture supernatants of the normal pancreatic duct cells and the blood should be examined by other analytical methods, but potential markers may be discovered by these approaches. In order to confirm its selective distribution, culture supernatants of other types of cancer cells could be analyzed in a similar manner.

Example 7

Analysis of Protein in the Supernatant of Cultured Cells Derived from Pancreatic Cancer The one-step sample preparation and protein chip mass spectrometry performed in Examples 4, 5 and 6 were modified, so that the number of supernatants of cells to be analyzed was increased: serum-free culture supernatants from 36 cell lines derived from pancreatic cancer, 10 cell lines derived from gastric cancer, 8 cell lines derived from colon cancer, 6 cell lines derived from breast cancer, 3 cell lines derived from prostate cancer, 9 other cell lines, 2 established cell lines derived from pancreatic ducts, and serum-free culture supernatant of primary cultured cells of the normal pancreatic duct were analyzed.

After aspirating the growth medium of the cells that were subjected to monolayer culture in a 10 cm culture dish, it is replaced with a warmed serum-free medium. After culturing for seven hours, the medium is removed, and the dish is washed three times in a phenol red-free RPMI 1640 medium. Then, 3.5 ml of the medium is added to the dish and cultured for 24 hours. After the conditioned medium is recovered and centrifuged, an equal amount of 1% acetic acid is added to the supernatant, and centrifuged again to prepare samples. Peptide of the samples is concentrated using Microcon-SCX (Millipore), a strong cation ion exchange membrane. After conditioning in methanol, undesired constituents were removed with 0.1% trifluoroacetic acid (TFA) and 10% acetonitrile (ACN).

The desired constituents are recovered with 250 μl of the elution buffer (50% ACN:40% water:10% ammonia K). Then organic solvents are evaporated using a centrifugation evaporator. The sample obtained is used for mass spectrometry. In order to find cell species-specific peaks, mass spectrometry is performed on the H4 protein chip (Ciphergen, Inc.). The chip is conditioned in 1 μl of 100% ACN, and further 1 μl of 0.5% TFA-containing water-ACN (50:50, v/v), and 2.5 μl of the above sample is added thereto. After drying, it is washed twice in 2.5 μl of water. As the matrix, α-cyano-4-hydroxy cinnamic acid (CHCA) is used. Mass spectra are formed according to the company's manual. After obtaining spectra for all samples, peaks are matched between cells with a mass error of 0.1%.

Figure 8:
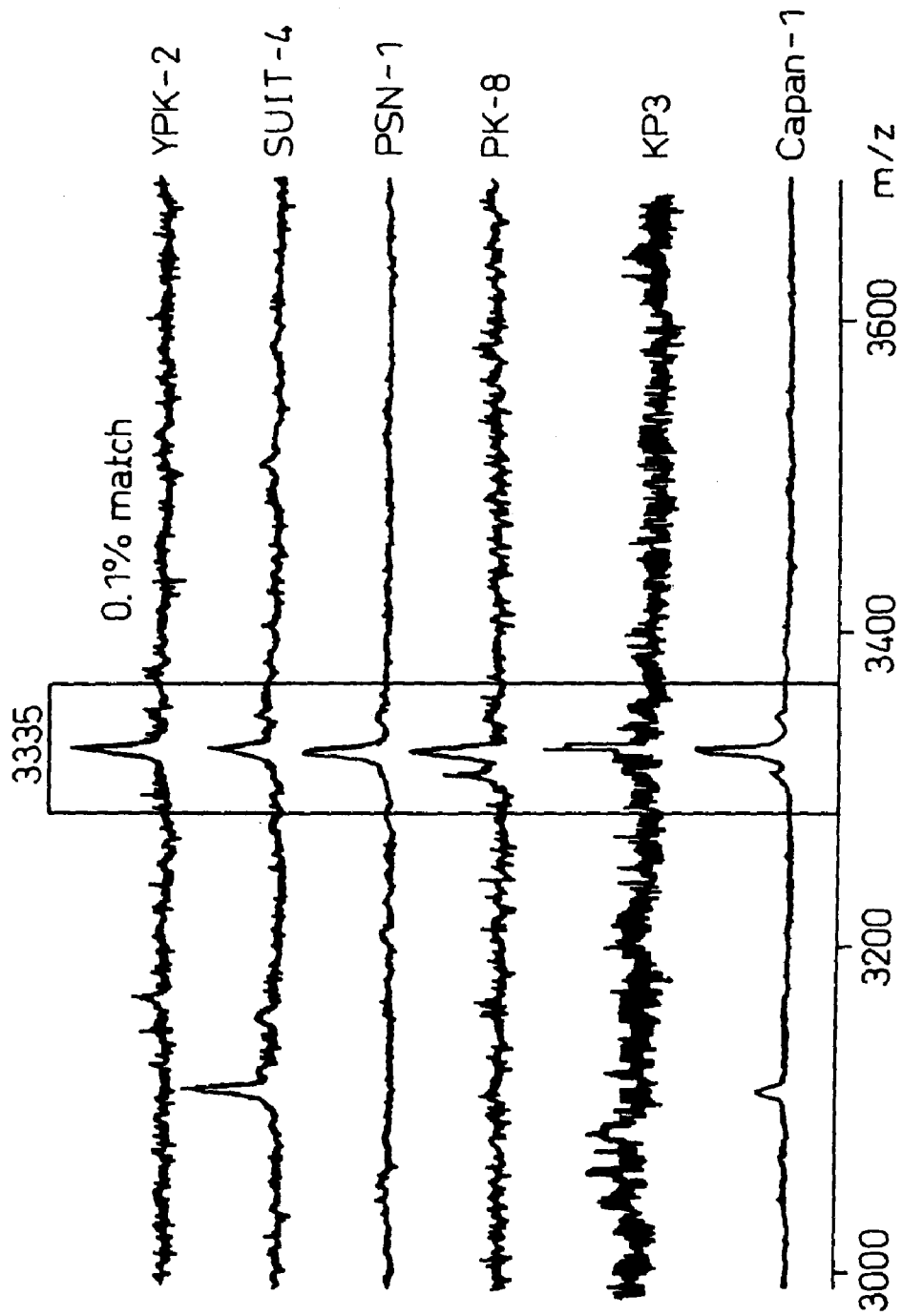
FIG. 8 shows mass spectra obtained from 6 subcultured cells derived from pancreatic cancer. The protocol was as described in Example 7.

Table 2 summarizes the molecular weight of peptides observed in 3 or more pancreatic cancer lines. Also, in six pancreatic cancer-derived cell lines, the mass spectra as shown in FIG. 8 were obtained. It was found that in the supernatants of pancreatic cancer-derived cell lines, a peptide peak of molecular weight of about 3335 specific for pancreatic cancer was observed that it could not be seen in the supernatants from other cancers.

TABLE 2

Comparison of low molecular weight peptides secreted from the subcultured cell lines derived from pancreatic cancer and other cancer-derived cell lines

| M/z | Pancreatic cancer-derived cell line (n = 36) | Pancreatic duct-derived cell line (n = 2) | Colon cancer-derived cell line (n = 8) | Breast cancer-derived cell line (n = 6) | Prostate cancer-derived cell line (n = 3) | Gastric cancer-derived cell line (n = 10) | Others (n = 9) |
|---|---|---|---|---|---|---|---|
| 2340.1 | 9 | — | — | — | — | — | — |
| 2427.3 | 14 | — | 4 | — | 1 | 3 | 2 |
| 2497.6 | 4 | — | — | 1 | — | — | — |
| 2597.6 | 6 | — | 2 | — | — | — | — |
| 2627.4 | 25 | 1 | 2 | 1 | 1 | 4 | 3 |
| 2732.6 | 15 | — | 3 | — | 1 | 1 | — |
| 2997.2 | 3 | 1 | — | 1 | — | — | — |
| 3105.2 | 4 | — | 1 | — | — | — | — |

TABLE 2-continued

Comparison of low molecular weight peptides secreted from the subcultured cell lines derived from pancreatic cancer and other cancer-derived cell lines

| M/z | Pancreatic cancer-derived cell line (n = 36) | Pancreatic duct-derived cell line (n = 2) | Colon cancer-derived cell line (n = 8) | Breast cancer-derived cell line (n = 6) | Prostate cancer-derived cell line (n = 3) | Gastric cancer-derived cell line (n = 10) | Others (n = 9) |
|---|---|---|---|---|---|---|---|
| 3232.2 | 3 | — | 1 | — | 1 | — | — |
| 3335.5 | 6 | — | — | — | — | — | — |
| 3802.8 | 8 | 1 | 2 | — | — | 1 | — |

S/N>3

Peaks detected in three or more pancreatic cancer lines are listed.

Example 8

Molecular Weight Determination and Identification of Substances Specifically Secreted from Pancreatic Cancer-derived Cells The monoisotopic mass of the peak found on the protein chip and the common MALDI plate in Example 7 was calculated to be 3334.737 Da by a quadruple hybrid type time-of-flight mass spectrometry (Sciex, Q-STAR). The peak was subjected to tandem mass spectrometry, and was found to correspond to the C-terminal fragment (DVGSYQEKVDV-VLGPIQLQTPPRREEEPR; SEQ ID NO:1) of the DMBT1 gene by the combined use of the mass tag method and the de novo sequencing method. The mass estimated from this sequence is 3334.739 Da. Furthermore, 5 ml of the culture supernatant of the CAPAN-1 cell line was partially purified by the above solid phase extraction method and gel filtration to prepare a sample. It was digested with lysil endopeptidase, and analyzed by the ion trap type tandem mass spectrometer, and the same result was obtained by a database search using Mascot and Sequest software.

Example 9

Effect of the Phenol Red-free Medium on Mass Spectrometry

CAPAN-1 cells were cultured in a standard RPMI medium containing phenol red or a phenol red-free RPMI medium, and 2 ml of the culture supernatant was adjusted to 50 µl by the sample preparation in Example 7. The prepared sample and a saturated CHCA solution were mixed at a ratio of 1:2, and 1 µl of it was added as it was to the MALDI plate. Then it was air-dried, and measured by voyager De Pro (Applied Biosystems). The instrument was operated according to the company's manual. For calibration, insulin B chain (monoisotopic mass 3493.65) was used as an external standard.

Figure 9:
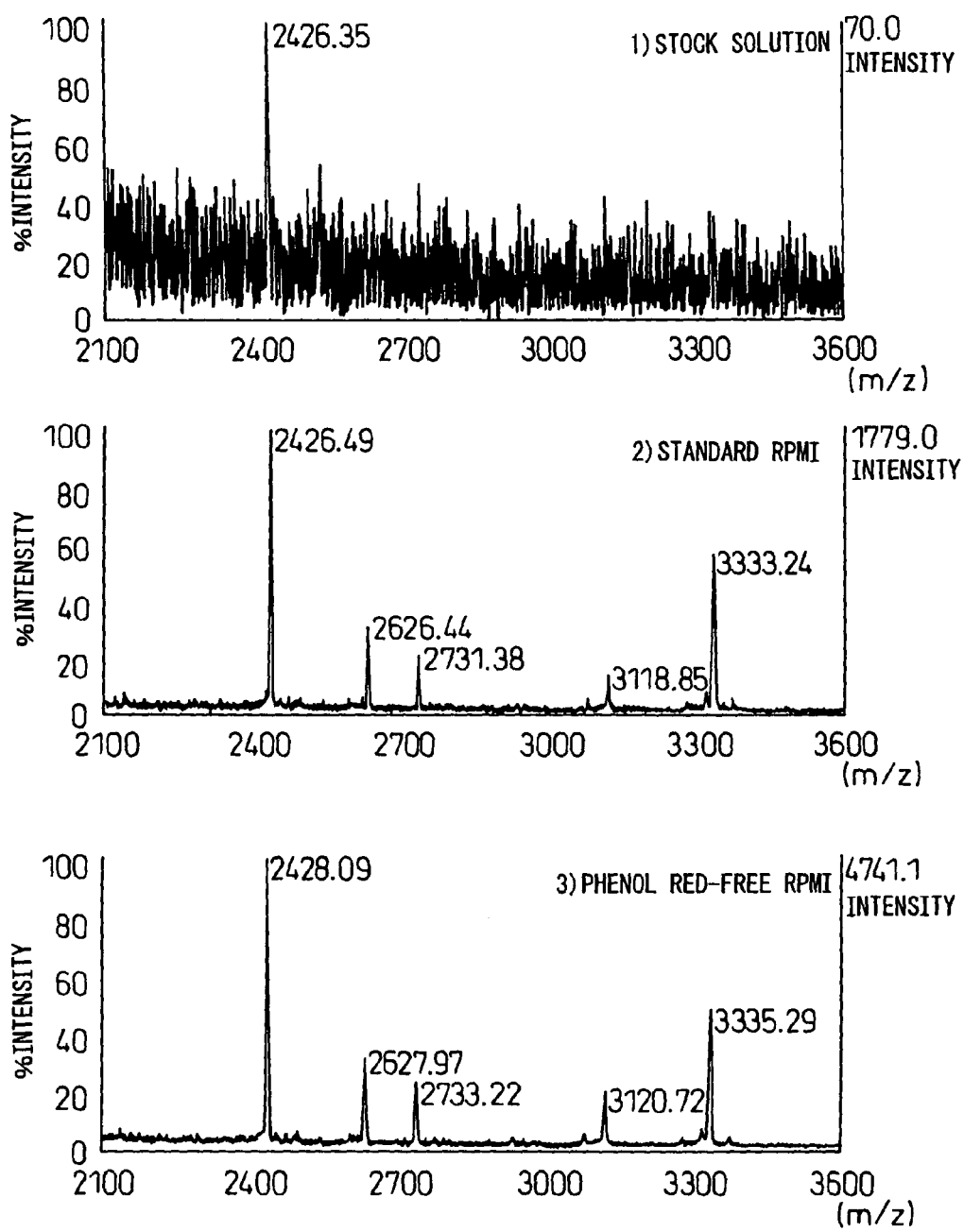
FIG. 9 shows a difference when samples were prepared from a culture supernatant with or without phenol red. It shows a chart obtained by analyzing, by MALDI, 1) 1 µl of the stock solution, 2) a 50 µl equivalent of the RPMI culture supernatant with phenol red, and 3) a 50 µl equivalent of the RPMI culture supernatant without phenol red.
Figure 10:
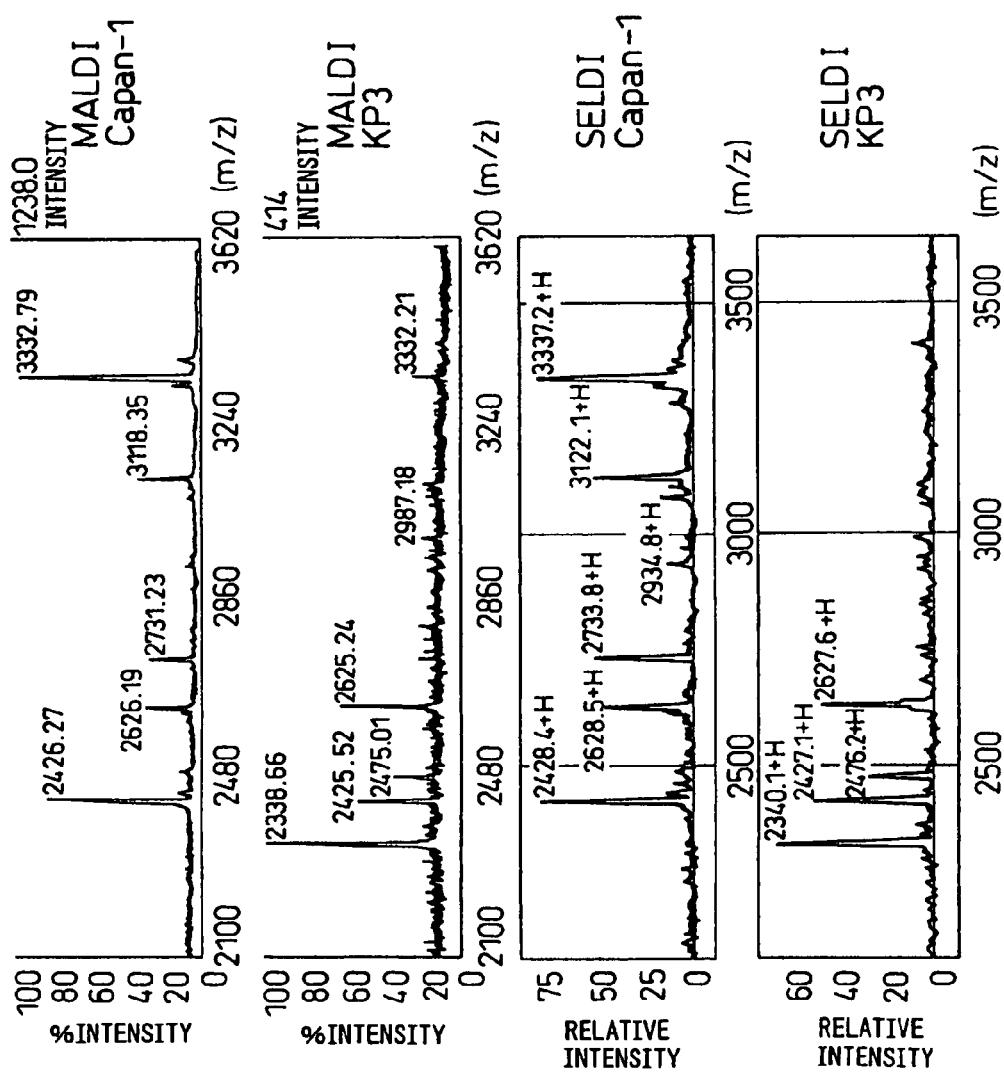
FIG. 10 shows results in which the culture supernatants of CapanI and KP3 were analyzed by SELDI and MALDI after sample preparation.

The results of analysis in which 1 µl of the stock solution of the culture supernatant of CAPAN-1 cultured in a standard RPMI medium and the culture supernatant of each medium were analyzed by MALDI are shown in FIG. 9. In comparison for the largest signal m/z 2426, the S/N ratio for the stock solution is 17.9, that of the prepared culture supernatant of the standard RPMI medium is 209.9, and that of the prepared culture supernatant of the phenol red-free medium is 331.1, indicating a gradual decrease in noise. Thus, it can be seen that the sample preparation of the present invention is useful as a pretreatment for mass spectrometric analysis, and by using a phenol red-free medium, further reduction in noise can be observed.

When the one-step sample preparation for low molecular weight peptides of the present invention is compared with other concentration methods, other methods have various problems: concentration by gel filtration takes a long time (about 3 hours for 2 ml), many peptides adsorb to the filtration membrane, and proteins having large molecular weight are concentrated at the same time, thereby hindering the detection of low molecular weight peptides in mass spectrometry. Furthermore, a concentration method combined with freeze-drying takes a long time (longer than half a day), sample volume cannot be reduced due to concentration of salts, and desalting by dialysis is cumbersome in processing and thus salts tend to remain as noise in mass spectrometry. In addition, proteins with large molecular weight are also concentrated, which could hinder the detection of peptides. In the one-step preparation of the present invention, 10 samples can be prepared within 2 hours and, thus, it is more suitable as pretreatment for mass spectrometry compared to other methods.

Example 10

Comparison of the Analysis by MALDI After One-step Sample Preparation with SELDI Two ml of the culture supernatants of CAPAN-1 cells and KP3 cells and KP3 cells in the phenol red-free medium was adjusted to 50 µl by the sample preparation in a similar manner to Example 9, which was mixed with the CHCA solution at a ratio of 1:2, and 1 µl of it was added as it was to the MALDI plate. Then it was air-dried and measured by voyager De Pro (Applied Biosystems). The instrument was operated according to the company's manual. For calibration, insulin B chain (monoisotopic mass 3493.65) was used as an external standard. Comparison with the analytical result with SELDI is shown in FIG. 9. By using the one-step sample preparation, analysis equal to or better than the analytical result with SELDI is also possible with MALDI. Comparison of peaks between a plurality of cell lines can also be performed by common software.

Example 11

Determination of Amino Acid Sequence of m/z 2340.1

A peak of m/z 2340.1 was recognized in 9 out of 36 pancreatic cancer cell lines in a method described in Example 7 as has been shown in Table 2. This result was checked by re-testing in which a peak of molecular weight m/z 2340.1 was obtained from the culture supernatant of cells of 11 out of 36 pancreatic cancer cell line. In Table 2, this peak was not detected from the culture supernatant of other cells, but when two more cell lines derived from gastric cancer were tested, a similar peak was obtained from one of them. Thus, from 11 of 36 cell lines derived from pancreatic cancer and one of 12 cell lines derived from gastric cancer, a molecular weight peak of m/z 2340.1 was detected, and from other cell lines derived from various organs described in Table 2 this peak was not detected. The cell lines derived from pancreatic cancer in which this m/z 2340.1 was detected were 11 cell lines: KLM-1, KMP3, KMP5, KP1N, KP2, KP3, PK-8, PK45P, PK-59, YPK-3, and Panc1.

When the above sample of m/z 2340.1 was subjected to tandem mass spectrometry, and determination of the amino acid sequence was attempted by combined use of the mass tag method and the de novo sequencing method, no amino acid sequence was analyzed. Thus, it was thought that two or more cysteine residues are present in the internal sequence of the peptide of interest and are bound via disulfide bonds, and the sample was reduction-alkylated according to a standard method. The reaction mixture was added to the H4 chip and subjected to mass spectrometry, and it was found that the peak of 2340.1 had disappeared and a peak of 2457 had appeared. From the difference of the masses, it was estimated that the peptide of interest has two cysteines in the molecule and is bound via disulfide bonds.

That the peptide of interest is not decomposed in the reaction was confirmed by the detection of the desired peak after reaction for the same period of time in a buffer containing no reduction-alkylating reagents. Thus, in order to subject this peak to tandem mass spectrometry, about 20 ml of serum-free culture supernatant was recovered from a cultured pancreatic cancer cell line KP3 by a method described in Example 7, and the peptide was prepared. The sample after reduction-alkylation was subjected to gel filtration chromatography to remove excess reagents. For the fraction of interest, tandem mass spectrum was measured by oMALDI-QSTAR (Applied Biosystems). When database search was performed using MASCOT, a MS/MS analysis software, C-terminal 20 amino acids, NCFAIRHFENKFAVETLICS (SEQ ID NO:2), of the integral membrane protein 2B became a high score.

Also in the analysis with Bioanalyst, a software attached to QSTAR, the sequence tag of RHFENK (SEQ ID NO: 5, also referred to as residues 6-11 of SEQ ID NO: 2) could be read, and it was found by a database search to correspond to the sequence of NCFAIRHFENKFAVETLICS (SEQ ID NO: 2). Furthermore, when a similar data search was performed with the ProteinProspector (UCSF) software, it was found to be a C-terminal 20 amino acids of the integral membrane protein 2B as with the above two softwares. Based on these analytical results, it was concluded that the sequence is NCFAIRHFENKFAVETLICS (SEQ ID NO: 2) and is crosslinked via two disulfide bonds (Biochemistry 40:3449-3457, 2001). The theoretical value for the monoisotopic mass is 2339.12 Da. The measured value was 2339.03 Da.

Incidentally, a peptide comprising 34 amino acids (Nature 399; 776-781, 1999) purified from amyloid lesion of familial British dementia completely contains this sequence. It has been reported that, in this family, the peptide related to dementia underwent mutation of the termination codon of the integral membrane protein 2B from TGA to AGA and thus 11 amino acids, RTVKKNIIEEN (SEQ ID NO:3), have been added downstream, and is secreted outside of the cell (Biochemistry 40:3449-3457, 2001).

However, there are no reports that pancreatic cancer is related to the integral membrane protein 2B gene, nor are there reports that 20 amino acids NCFAIRHFENKFAVETLICS (SEQ ID NO:2) at the C-terminal end of the wild type integral membrane protein 2B peptide has been released in the culture supernatant of subcultured cells derived from pancreatic cancer. This peptide has been specifically secreted from subcultured cells derived from pancreatic cancer, and thus it is likely to be specifically detected in the body fluids such as blood and urine or cancer tissues of pancreatic cancer patients. This indicates that the detection of this peptide comprising 20 amino acids is useful for early discovery of pancreatic cancer and as a marker for treatment. Similar applications may be conceived as for the C-terminal 29 amino acids of the peptide encoded by the DMBT1 gene described above in Detailed Explanation.

Example 12

Obtaining Antibody to the C-terminal Peptide of DMBT1

As antibody to DMBT1, a monoclonal antibody to 26-40 amino acids at the N-terminal end of DMBT1 has been reported (Mollenhauer, J. et al., Cancer Res., 60:1704-1710, 2000). However, there are no reports of other antibodies. An amino acid LQTPPRREEEPR (SEQ ID NO: 4, also referred to as residues 18-29 of SEQ ID NO: 1) corresponding to the 2415-2426 amino acids of DMBT1 of the 29-amino acid sequence at the C-terminal end of DMBT1 of which amino acid sequence was determined in Example 8 was peptide-synthesized according to a standard method, and then was bound to keyhole limpet hemocyanin (KLH), with which two rabbits were immunized three times according to a standard method. The serum was used in the subsequent experiment as the L129 antiserum.

Example 13

Confirmation of Peptide in the Cell Supernatant by Immunoprecipitation SELDI MS

Using antibody obtained in Example 12, the peptide in the supernatant of pancreatic cancer-derived cells was immunologically identified. 500 µl of the cell supernatant was reacted overnight with a 100-fold diluted L129 antiserum at 4° C. Then, it was reacted with 20 µl of Protein G Sepharose (Pharmacia) for 30 minutes. After washing five times in PBS, the bound material was eluted in 10 µl of 0.2% TFA. Four µl of the eluted solution was used for analysis using the SELDI H4 chip.

Figure 11:
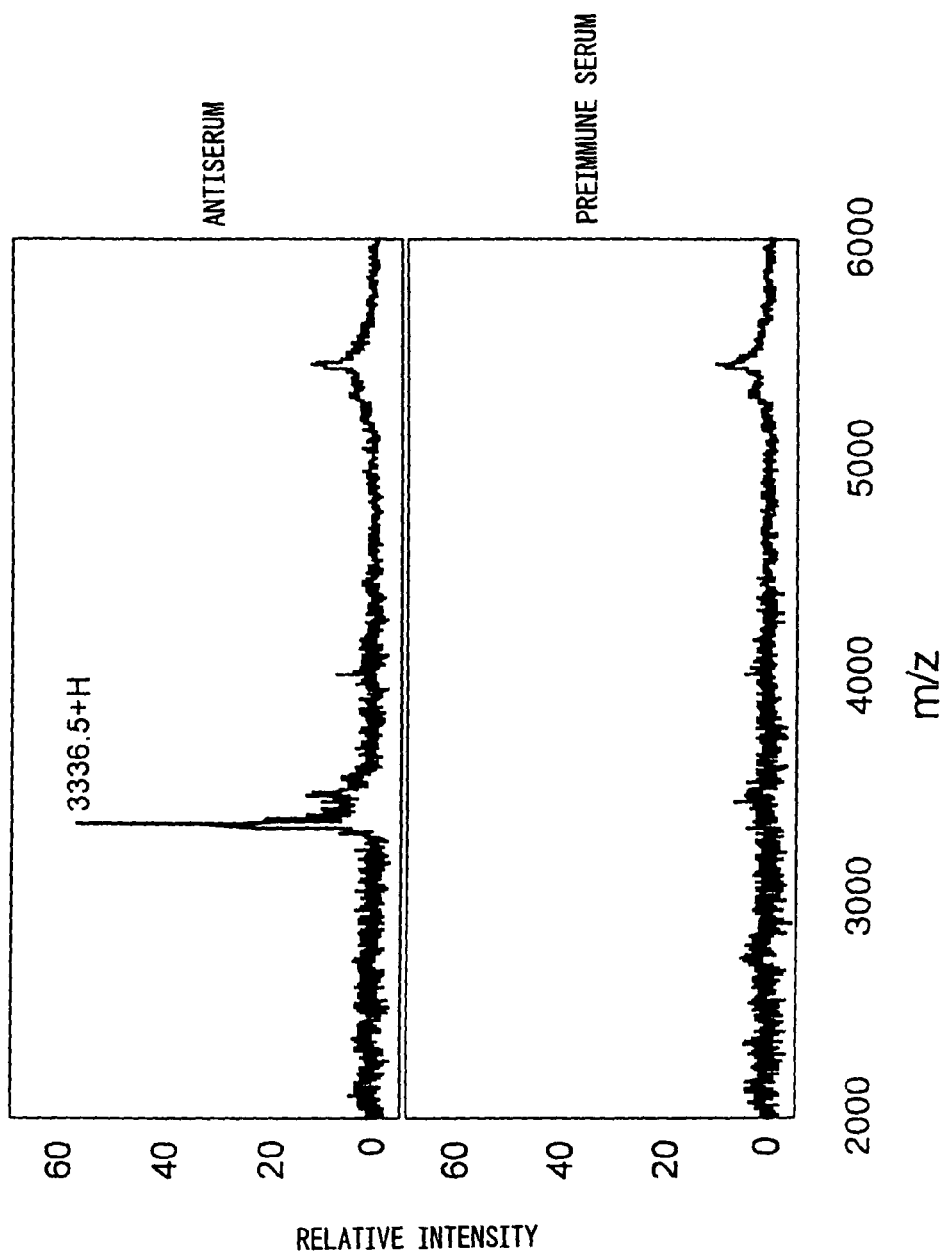
FIG. 11 shows results in which the supernatant of Capan-1 cells was immunoprecipitated with a serum to a peptide LQT-PPRREEEPR (SEQ ID NO: 4, also referred to as residues 18-29 of SEQ ID NO: 1) corresponding to amino acids 2415-2426 of DMBT1 and with a preimmune antiserum which is a negative control, and then was subjected to mass spectrometry by the SELDI H4 chip.
Figure 12:
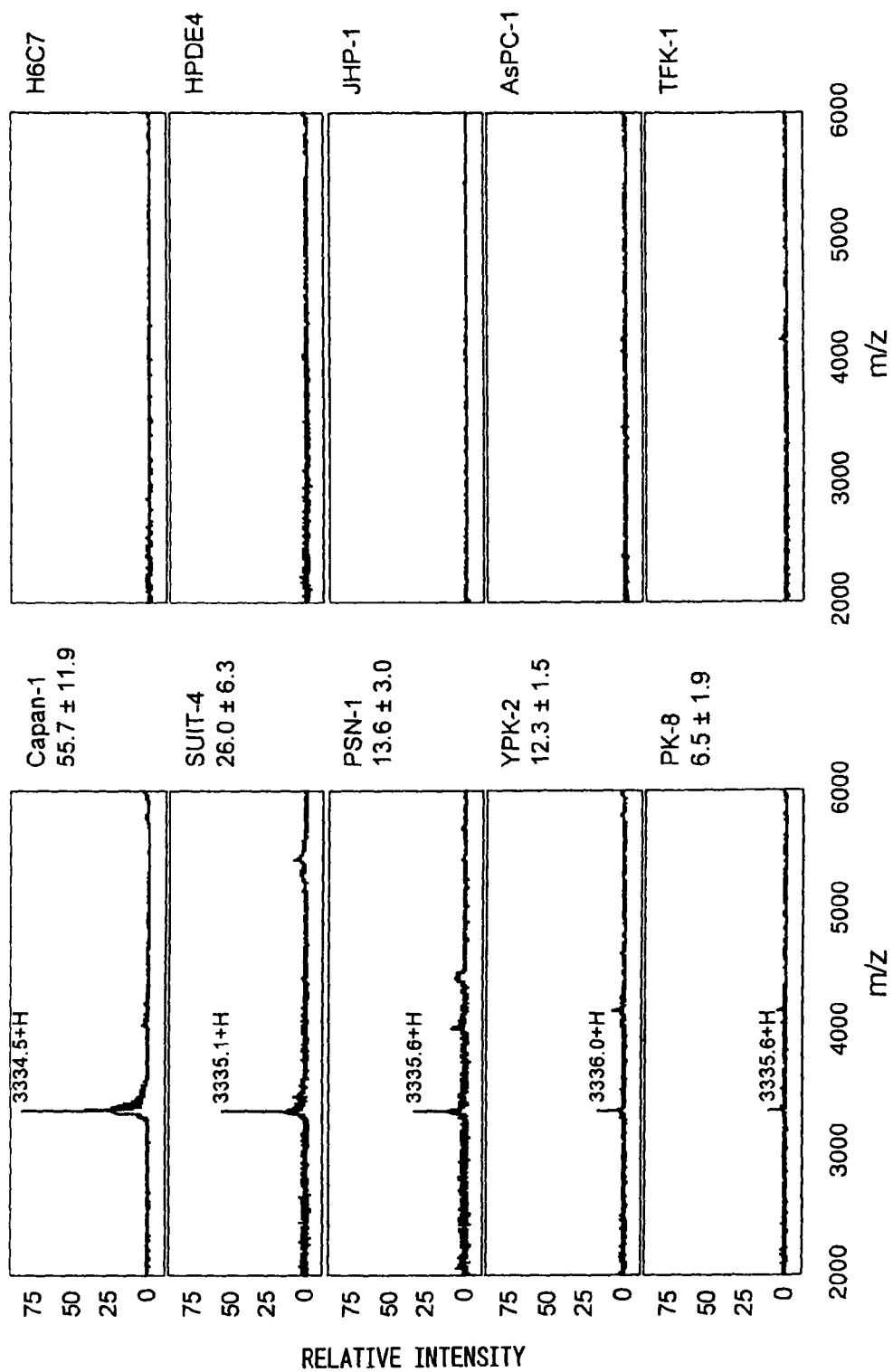
FIG. 12 shows results in which the supernatants of Capan-1, SUIT-4, PSN-1, YPK-2 AND PK-1 cells were immunoprecipitated with the L129 antiserum, and then was subjected to mass spectrometry with the SELDI H4 chip.

As a result, the culture supernatant of Capan-1 cultured in the presence of 10% FCS was immunoprecipitated with the L129 antiserum, and a peak of m/z 3335 was detected by analysis with SELDI MS as shown in FIG. 11, whereas the peak of m/z 3335 was not detected for the preimmune antiserum used as the control. As shown in FIG. 12, the peak of m/z 3335 was also detected for the culture supernatant of SUIT-4, PSN-1, YPK-2, PK-1 cells by immunoprecipitation using the L129 antiserum, but not detected from the supernatants of other cultured cells. This result is consistent with that in Example 7 and FIG. 8.

It is clear that the antibody obtained here recognizes the 29 amino acids at the C-terminal end of DMBT1. By using this antibody as a probe, it is possible to capture and detect the 29 amino acids at the C-terminal end of DMBT1 from test samples such as human serum, urine, and tissues. Also, by detecting the 29 amino acids at the C-terminal end of DMBT1 using this antibody, it can be used for diagnosis of pancreatic cancer patients based on early discovery or as a prognostic marker for evaluating therapeutic effect. In this Example, though antibody was created to LQTPPRREEEPR (SEQ ID NO: 4, also referred to as residues 18-29 of SEQ ID NO: 1) corresponding to the 2415-2426 amino acids of DMBT1, antibody to the 29 amino acids at the C-terminal end of DMBT1 as set forth in SEQ ID NO: 1 can also be used.

Example 14

Western Blotting of DMBT1 with the L129 Antiserum

Figure 13:
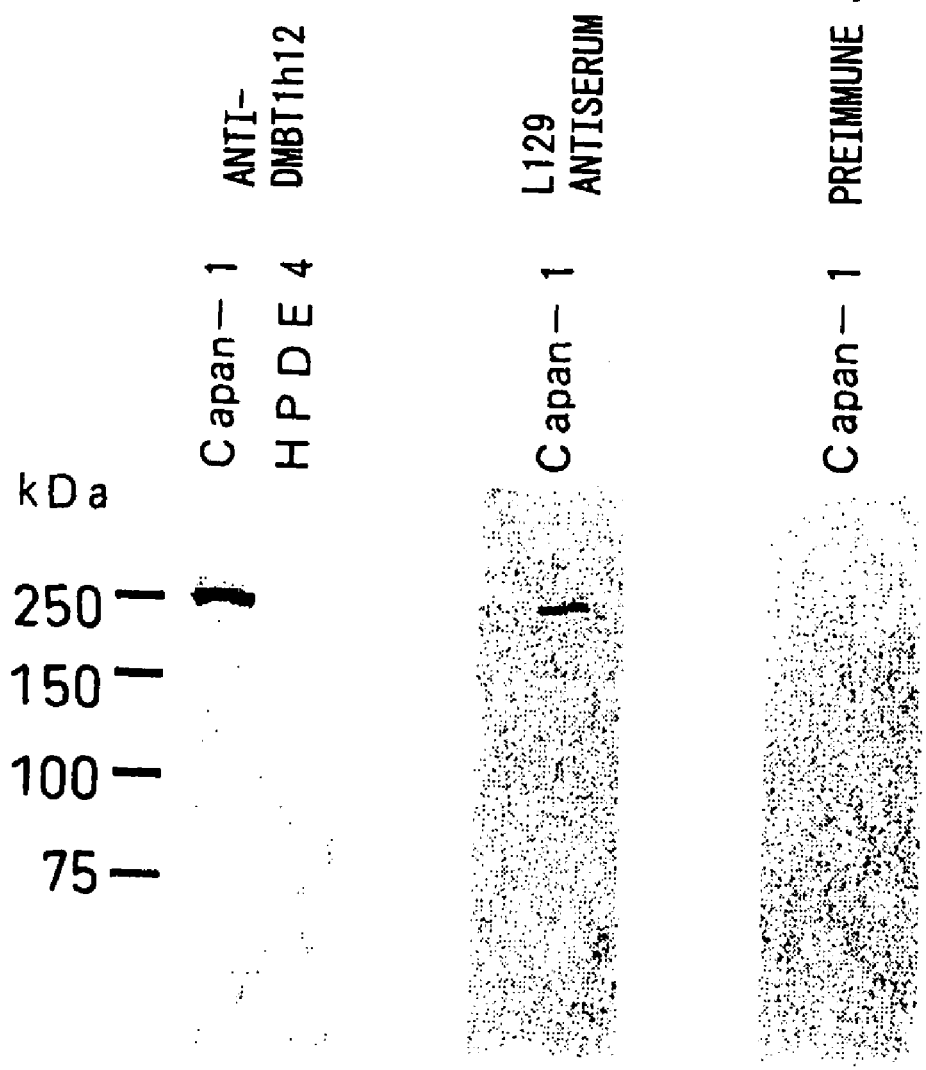
FIG. 13 shows results in which the lysate of Capan-1 cells was subjected to Western blot analysis with the L129 antiserum.

In order to examine the cellular expression of the DMBT1 protein, Western blotting was performed according to a method by Mollenhauer (Cancer Res., 60:1704-1710, 2000). The cell lysate of the Capan-1 cells was electrophoresed on a SDS-PAGE gel. The protein was transferred to an Immobilon PVDF membrane, and was detected using the L129 antiserum. As shown in FIG. 13, the L129 antiserum recognizes a protein of 2426 amino acids of full-length DMBT1. It is clear that this antibody can bind to the full-length or the C-terminal 29 amino acids if it is DMBT1 containing LQTPPRREEEPR (SEQ ID NO: 4, also referred to as residues 18-29 of SEQ ID NO: 1) corresponding to the 2415-2426 amino acids of DMBT1, and even when degradation products of DMBT1 containing the C-terminal 29 amino acids are present in test samples, detection can be effected using this antibody as a probe.

The invention claimed is:

1. A secretory peptide consisting of the amino acid sequence as set forth in SEQ ID NO: 2.

2. A diagnostic kit comprising the peptide according to claim 1, which diagnoses pancreatic cancer by detecting or quantitating the peptide according to claim 1.

* * * * *

SEQUENCE LISTING

```
<160> NUMBER OF SEQ ID NOS: 5

<210> SEQ ID NO 1
<211> LENGTH: 29
<212> TYPE: PRT
<213> ORGANISM: Homo sapiens

<400> SEQUENCE: 1

Asp Val Gly Ser Tyr Gln Glu Lys Val Asp Val Val Leu Gly Pro Ile
 1               5                  10                  15

Gln Leu Gln Thr Pro Pro Arg Arg Glu Glu Pro Arg
            20                  25

<210> SEQ ID NO 2
<211> LENGTH: 20
<212> TYPE: PRT
<213> ORGANISM: Homo sapiens

<400> SEQUENCE: 2

Asn Cys Phe Ala Ile Arg His Phe Glu Asn Lys Phe Ala Val Glu Thr
 1               5                  10                  15

Leu Ile Cys Ser
            20

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Thr Val Lys Lys Asn Ile Ile Glu Glu Asn
 1               5                  10

<210> SEQ ID NO 4
<211> LENGTH: 12
<212> TYPE: PRT
<213> ORGANISM: Homo sapiens

<400> SEQUENCE: 4

Leu Gln Thr Pro Pro Arg Arg Glu Glu Pro Arg
 1               5                  10

<210> SEQ ID NO 5
<211> LENGTH: 6
```

```
<212> TYPE: PRT
<213> ORGANISM: Homo sapiens

<400> SEQUENCE: 5

Arg His Phe Glu Asn Lys
 1               5
```